United States Patent
McKie et al.

(10) Patent No.: US 6,620,838 B1
(45) Date of Patent: Sep. 16, 2003

(54) BENZOPYRAZONE COMPOUNDS, COMPOSITIONS THEREOF, AND METHODS OF TREATMENT THEREWITH

(75) Inventors: Jeffrey A. McKie, San Diego, CA (US); Shripad S. Bhagwat, San Diego, CA (US); Johanne Renaud, Basil (CH); Martin Missbach, Basil (CH)

(73) Assignee: Signal Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/125,965

(22) Filed: Apr. 19, 2002

(51) Int. Cl.$^7$ .................. A61K 31/4025; C07D 405/10
(52) U.S. Cl. ........................ 514/422; 548/525
(58) Field of Search ............................ 548/525; 514/422

(56) References Cited

U.S. PATENT DOCUMENTS

| | | |
|---|---|---|
| 6,291,456 B1 | 9/2001 | Stein et al. |
| 6,331,562 B1 | 12/2001 | Bhagwat et al. |

OTHER PUBLICATIONS

Al–Shaffar et al., 1996, "Assessment of the role of GM–CSF in the cellular transformation and the development of erosive lesions around orthopaedic implants", Am J Clin Pathol. 105(5):628–39.

Alonzi et al., 1998, "Interleukin 6 is required for the development of collagen–induced arthritis", J Exp Med. 187(4):461–8.

Barkhelm et al., 1998, "Differential response of estrogen receptor alpha and estrogen receptor beta to partial estrogen agonists/antagonists", Mol Pharmacol. 54(1):105–12.

Bismar et al., 1995, "Increased cytokine secretion by human bone marrow cells after menopause or discontinuation of estrogen replacement", J Clin Endocrinol Metab. 80(1):3351–5.

Bodine et al., 1998, "Estrogen receptor–alpha is developmentally regulated during osteoblast osteoblast differentiation and contributes to selective responsiveness of gene expression", Endocrinology. 139(4):2048–57.

Brandenberger et al., 1998, "Estrogen receptor alpha (ER–alpha) and beta (ER–beta) mRNAs in normal ovary, ovarian serous cystadenocarcinoma and ovarian cancer cell lines: down–regulation of ER–beta in neoplastic tissues", J Clin Endocrinol Metab. 83(3):1025–8.

Chen et al., 2001, "Molecular basis for the constitutive activity fo estrogen–related receptor alpha–1", J Biol Chem. 276(30):28465–70.

Chung et al., 2002, "Resistance to tamoxifen–induced apoptosis is associated with direct interaction between Her2/neu and cell membrane estrogen receptor in breast cancer", Int J Cancer. 97(3):306–12.

Clinton and Hua, 1997, "Estrogen action in human ovarian cancer", Crit Rev Oncol Hematol. 25(1):1–9.

Cooke et al., 1998, "Mechanism of estrogen action: lessons from the estrogen receptor–alpha knockout mouse", Biol Reprod. 59(3):470–5.

Couse et al., 1997, "Tissue distribution and quantitative analysis of estrogen receptor–alpha (ERalpha) and estrogen receptor–beta (ERbeta) messenger ribonucleic acid in the wild–type and ERalpha–knockout mouse", Endocrinology. 138(11):4613–21.

Coward et al., 2001, "4–Hydroxytamoxifen binds to and deactivatess the estrogen–related receptor gamma", Proc Natl Acad Sci U S A. 98(15):8880–4.

Das et al., 1997, "Estrogenic responses in estrogen receptor–α deficient mice reveal a distinct estrogen signaling pathway", Proc. Natl. Acad. Sci. USA 94:12786–91.

Devlin et al., 1998, "IL–6 mediates the effects of IL–1 or TNF, but not PTHrP or 1,25(OH)2D3, on osteoclast–like cell formation in normal human bone marrow cultures", J Bone Miner Res. Mar. 1998;13(3):393–9.

Duan et al., 1998, "Estrogen–induced c–fos protooncogene expression in MCF–7 human breast cancer cells: role of estrogen receptor Sp1 complex formation", Endocrinology. 139(4):1981–90.

Enmark et al., 1997, "Human estrogen receptor beta–gene structure, chromosomal localization, and expression pattern", J Clin Endocrinol Metab. 82(12):4258–65.

Eustace et al., 1993, "Interleukin–6 (IL–6) functions as an autocrine growth factor in cervical carcinomas in vitro", Cynecol Oncol. 50(1):15–19.

(List continued on next page.)

*Primary Examiner*—Joseph K. McKane
*Assistant Examiner*—Sonya Wright
(74) *Attorney, Agent, or Firm*—Pennie & Edmonds LLP

(57) ABSTRACT

Benzopyranone compounds having the following structure:

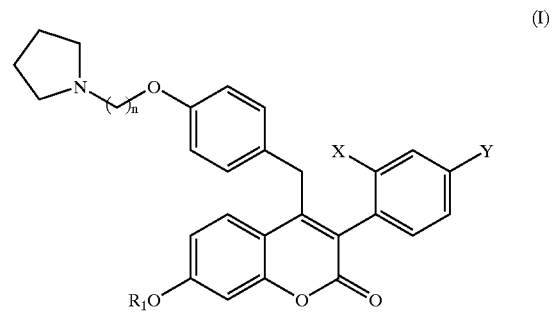

wherein $R_1$, X, Y and n are as defined here, are disclosed. The compounds of formula (I), wherein $R_1$ is H, can be prepared by demethylation of the corresponding phenolic methyl ether. The compounds are useful for treating a bone-resorbing disease, cancer, arthritis or an estrogen-related condition such as breast cancer, osteoporosis and endometriosis.

33 Claims, No Drawings

OTHER PUBLICATIONS

Farhat et al., 1996, "The vascular protective effects of estrogen", FASEB J. 10(5):615–24.

Garrett et al., 1997, "A murine model of human myeloma bone disease", Bone 20(6):515–20.

Girasole et al., 1992, "17 beta–estradiol inhibits interleukin–6 production by bone marrow–derived stromal cells and osteoblasts in vitro: a potential mechanism for the antiosteoporotic effect of estrogens", J Clin Invest. 89(3):883–91.

Grese et al., 1997, "Structure–activity relationships of selective estrogen receptor modulators: modifications to the 2–arylbenzothiopene core of raloxifene", J Med Chem. 40(2):146–67.

Gupta et al., 1985, "7–hydroxy–4–phenyl–3(4–hydroxyphenyl)–coumarin—a new interceptive agent", Indian J Exp Biol. 23(11):638–40.

Gustafsson et al., 1998, "Therapeutic potential of selective estrogen receptor modulators", Curr Opin Chem Biol. 2(4):508–11.

Hata et al., 1998, "Role of estrogen and estrogen–related growth factor in the mechanism of hormone dependency endometrial carcinoma cells", Oncology. 55 Suppl 1:35–44.

Hughes et al., 1996, "Estrogen promotes apoptosis of murine osteoclasts mediated by TGF–beta", Nat Med. 2(10):1132–6.

Iafrati et al., 1997, "Estrogen inhibits the vascular injury response receptor alpha–deficient mice", Nat Med. 3(5):545–8.

Jansson et al., 1994, "Estrogen induces a potent suppression of experimental autoimmune encephalomyelitis and collagen–induced arthritis in mice", J Neuroimmunol. 53(2):203–7.

Jeltsch et al., 1987, "Structure of the human oestrogen–responsive gene pS2", Nucleic Acids Res. 15(4):1401–14.

Jilka et al., 1992, "Increased osteoclast development after estrogen loss: mediation by interleukin–6", Science 57(5066):88–91.

Kelly et al., 1999, "Estrogen Modulation of G–protein–coupled Receptors", Trends Endocrinol Metab. 10(9):369–374.

Kimble et al., 1996, "Estrogen deficiency increases the ability of stromal cells to support murine osteoclastogenesis via an interleukin–1and tumor necrosisfactor–mediatedstimulation of macrophage colony–stimulating factor production", J Biol Chem. 271(46):28890–7.

Kimble et al., 1995, "Simultaneous block of interleukin–1 and tumor necrosis factor is required to completely prevent bone loss in the early postovariectomy period", Endocrinology. 136(7):3054–61.

Klein et al., 1991, "Murine anti–interleukin–6 monoclonal antibody therapy for a patient with plasma cell leukemia", Blood. 78(5):1198–204.

Klein et al., 1989, "Paracrine rather than autocrine regulation of myeloma–cell growth and differentiation by Interleukin–6", Blood. 73(2):517–26.

Koo et al., 1992, "Interleukin–6 and renal cell cancer: production, regulation, and growth effects", Cancer Immunol Immunother. 35(2):97–105.

Korach et al., 1994, "Insights from the study of animals lacking functional estrogen receptor", Science 266(5190):1524–7.

Krege et al., 1998, "Generation and reproductive phenotypes of mice lacking estrogen receptor beta", Proc Nat Acad Sci U S A.95(26):15677–82.

Kulper et al., 1997, "Comparison of the ligand binding specificity and transcript tissue distribution of estrogen receptors alpha and beta", Endocrinology. Mar. 1997; 138(3):863–70.

Kurihara et al., 1989, "Generation of osteoclasts from isolated hermatopoietic cells", Blood 74(4):1295–302.

Laflamme et al., 1998, "Expression and neuropeptidergic characterization of estrogen receptors (ERalpha and ERbeta) throughout the rat brain: anatomical evidence of distinct roles of each subtype", J Neurobiol. 36(3):357–78.

Lednicer et al., 1965, "Mammalian Antifertility Agents: Basic Ethers of 3,4–Dephenylcoumarin", J. Med. Chem. 8:725–726.

Leisten Interleukin–6 serum levels correlate with footpad swelling in adjuvant–induced arthritic Lewis rats treated with cyclosporin A or indomethacin. Clin Immunol Immunopathol. Jul. 1990;56(1):108–15.

Levin et al., 1999, "Cellular Functions of the Plasma Membrane Estrogen Receptor", Trends Endocrinol Metab. 10(9):374–377.

Lorenzo et al., 1987, "Colony–stimulating factors regulate the development of multinucleated osteoclasts from recently replicated cells in vitro", J Clin Invest. 80(1):160–4.

Lu et al., 2001, "Transcriptional regulation of the estrogen–inducible pS2 breast cancer marker gene by the ERR family of orphan nuclear receptors", Cancer Res. 15; 61(18):6755–61.

MacDonald et al., 1986, "Effects of human recombinant CSF–GM and highly purified CSF–1 on the formation of multincleated cells with osteoclast characteristics in long–term bone marrow cultures", J Bone Miner Res. 1(2):227–33.

Martinez–Maza et al., 1992, "IL6 and AIDS", Res Immunol. 143(7):764–9.

Micheli et al., 1962, "Coumestrol, Plant Phenolics, and Synthetic Estrogens: a Correlation of Structure and Activity", 321–335.

Nadal et al., 2001, "The plasma membrane estrogen receptor: nuclear or unclear?", Trends Pharmacol Sci. 22(12):597–9.

Ogawa et al., 1997, "Behavioral effects of estrogen receptor gene distribution in male mice", Proc Natl Acad Sci U S A. 94(4):1476–81.

Ohshima et al., 1998, "Interleukin 6 plays a key role in the development of antigen–induced arthritis ", Proc Natl Acad Sci U S A. 95(14):8222–6.

Okamoto et al., 1997, "Interleukin–6 as a paracrine and autocrine growth factor in human prostatic carcinoma cells in vitro", Cancer Res. 57(1):141–6.

Okamoto et al., 1997, "Autocrine effect of androgen on proliferation of an androgen responsive prostatic carcinoma cell line, LNCAP: role of interleukin–6", Endocrinology. 138(11):5071–4.

Pacifici 1996, "Estrogen, cytokines, and pathogenesis of postmenopausal osteoporosis", J Bone Miner Res. 11(8):1043–51.

Paech et al., 1997, "Differential ligand activation of estrogen receptors ERalpha and ERbeta at AP1 sites", Science. 277(5331):1508–10.

Parfitt et al., 1996, "A new model for the regulation of bone resorption, with particular reference to the effects of bisphosphonates", J Bone Miner Res. 11(2):150–9.

Passeri et al., 1993, "Increased interleukin–6 production by murine bone marrow and bone cells after estrogen withdrawal", Endocrinology, 133(2):822–8.

Poli et al., 1994, "Interleukin–6 deficient mice are protected from bone loss caused by estrogen depletion", EMBO J. 13(5):1189–96.

Pollard et al., 1968, "The oestrogenic and anti–oestrogenic activity of some synthetic steroids and non–steroids", Steroids.

Ray et al., 1987, "Enhanced antifertility activity of non–steroidal molecules 3–n–butylamino–2–hydroxypropyloxy side chain", Contraception.35(3):283–7.

Reddy et al., 1994, "Interleukin–6 antisense deoxyoligonucleotides inhibit bone resorption by giant cells from human giant cell tumors of bone", J Bone Miner Res. 9(5):753–7.

Rissman et al., 1997, "Estrogen receptors are essential for female sexual receptivity", Endocrinology 138(1):507–10.

Rissman et al., 1997, "Estrogen receptor function as revealed by knockout studies: neuroendocrine and behavioralaspects", Horm Behav. 31(3):232–43.

Rohlff et al., 1998, "Estrogen cancer cell growth inhibition by tamoxifen is associated with inhibition of protein kinase C and induction of p21(waf1/cip1)", Prostate. 37(1):51–9.

Sar et al., 1999, "Differential expression of estrogen receptor–beta and estrogen receptor–alpha in the rat ovary", Endocrinology. 140(2):963–71.

Schiller et al., 1997, "17Beta–estradiol antagonizes effects of 1alpha,25–dihydroxyvitamin D3 on interleukin–6 production and osteoclast–like cell formation in mouse bone marrow primary cultures", Endocrinology 138(11):4567–71.

Shinar et al., 1990, "The effect of hemopoietic growth factors on the generation of osteoclast–like cells in mouse bone marrow cultures", Endocrinology 126(3):1728–35.

Shughrue et al., 1997, "Responses in the brain of estrogen receptor alpha–disrupted mice", Proc Natl Acad Sci USA. 94(20):11008–12.

Shughrue et al., 1997, "The distribution of estrogen receptor–beta mRNA in forebrain regions of the estrogen receptor–alpha knockout mouse", Endocrinology. 138(12):5649–52.

Shughrue et al., 1997, "Comparative distribution of estrogen receptor–alpha and –beta mRNA in the rat central nervous system", J Comp Neurol. 388(4):507–25.

Siegall et al., 1990, "Expression of the interleukin 6 receptor and interleukin 6 in prostate carcinoma cells", Cancer Res. 50(24):7786–8.

Simpson et al., 1998, "Estrogen regulation of transforming growth factor–alpha in ovarian cancer", J Steroid Biochem Mol Biol. 64(3–4):137–45.

Stein et al., 1995, "Repression of the interleukin–6 promoter by estrogen receptor by NF–kappa B and C/EBP beta", Mol Cell Biol. 15(9):4971–9.

Suzuki et al., 1996, "Calcitonin–induced changes in the cytoskeleton are mediated by a signal pathway associated with protein kinase A in osteoclasts", Endocrinology. 137(11):4685–90.

Tartour et al., 1994, "Analysis of interleukin 6 gene expression in cervical neoplasia using a quantitative polymerase chain reaction assay: evidence for enhanced interleukin 6 gene expression in invasive carcinoma", Cancer Res. 54(23):6243–8.

Tremblay et al., 2001, 4–Hydroxytamoxifen is an isoform–specific inhibitor of orphan estrogen–receptor–related (ERR) nuclear receptors beta and gamma. Endocrinology 142(10):4572–5.

Tremblay et al., "EM–800, a novel antiestrogen, acts as a pure antagonist of the transcriptional functions of estrogen receptors alpha and beta", Endocrinology 139(1):111–8, 1998.

Tsukamoto et al., 1992, "Interleukin–6 in renal cell carcinoma", J. Urol. 148(6):1778–81; discussion 1781–2.

Turner et al., 1998, "Differential responses of estrogen target tissues in rats including bone to clomiphene, enclomiphene, and zuclomiphene", Endocrinology. 139(9):3712–20.

Verma et al., 1993, "Microwave induced alteration in the neuron specific enolase gene expression", Indian J. Chem. 32B:239–243.

Weissglas et al., 1997, "The role of interleukin–6 in the induction of hypercalcemia in renal cell carcinoma transplanted into nude mice", Endocrinology 138(5):1879–85.

Wendling et al., 1993, "Treatment of severe rheumatoid arthritis by anti–interleukin 6 monoclonal antibody", J Rheumatol. 20(2):259–62.

Wyckoff et al., 2001, "Plasma membrane estrogen receptors are coupled to endothelial nitric–oxide synthase through Galpha(i)", J Biol Chem. 276(29):27071–6.

Yamashita et al., 1998, "Endocrine therapy in pancreatic carcinoma", Oncology. 55 Suppl 1:17–22.

Zhang et al., 1989, "Interleukin–6 is a potent myeloma–cell growth factor in patients with aggressive multiple myeloma", Blood. 74(1):11–3.

BENZOPYRAZONE COMPOUNDS, COMPOSITIONS THEREOF, AND METHODS OF TREATMENT THEREWITH

FIELD OF THE INVENTION

This invention is generally directed to benzopyranone compounds, compositions comprising the benzopyranone compounds and methods for treating a bone-resorbing disease, cancer, arthritis or an estrogen-related condition, comprising administering an effective amount of a benzopyranone compound to a patient in need thereof.

BACKGROUND OF THE INVENTION

The estrogen hormone has a broad spectrum of effects on tissues in both females and males. Many of these biological effects are positive, including maintenance of bone density, cardiovascular protection, central nervous system (CNS) function, and the protection of organ systems from the effects of aging. However, in addition to its positive effects, estrogen also is a potent growth factor in the breast and endometrium that increases the risk of cancer.

Until recently, it was assumed that estrogen binds to a single estrogen receptor (ER) in cells. As discussed below, this simple view changed significantly when a second ER (ER-β) was cloned (with the original ER being renamed ER-α), and when co-factors that modulate the ER response were discovered. Ligands can bind to two different ERs which, in the presence of tissue-specific co-activators and/or co-repressors, bind to an estrogen response element in the regulatory region of genes or to other transcription factors. Given the complexity of ER signaling, along with the tissue-specific expression of ER-α and ER-β and its co-factors, it is now recognized that ER ligands can act as estrogen agonists and antagonists that mimic the positive effects, or block the negative effects, of estrogen in a tissue-specific manner. This has given rise to the discovery of an entirely new class of drugs, referred to as Selective Estrogen Receptor Modulators or SERMs. These drugs have significant potential for the prevention and/or treatment of cancer and osteoporosis, as well as cardiovascular diseases and neurodegenerative diseases such as Alzheimer's disease.

Bone-resorbing diseases, such as osteoporosis, are debilitating conditions which affect a wide population, and to which there is only limited treatment. For example, osteoporosis affects about 50% of women, and about 10% of men, over the age of 50 in the United States. In individuals with osteoporosis, increased loss of bone mass results in fragile bones and, as a result, increased risk of bone fractures. Other bone-resorption diseases, such as Paget's disease and metastatic bone cancer, present similar symptoms.

Bone is a living tissue which contains several different types of cells. In healthy individuals, the amount of bone made by the osteoblastic cells is balanced by the amount of bone removed or resorbed by the osteoclastic cells. In individuals suffering from a bone-resorbing disease, there is an imbalance in the function of these two types of cells. Perhaps the most well known example of such an imbalance is the rapid increase in bone resorption experienced by postmenopausal women. Such accelerated bone lose is attributed to estrogen deficiency associated with menopause. However, the mechanism of how the loss of estrogen results in increased bone resorption has long been debated.

Recently, investigators have suggested that an increase in bone-resorbing cytokines, such as interleukin-1 (IL-1) and tumor necrosis factor (TNF), may be responsible for post-menopausal bone loss (Kimble et al., *J. Biol. Chem.* 271:28890–28897, 1996), and that inhibitors of these cytokines can partially diminish bone loss following ovariectomy in rodents (Pacifici, *J. Bone Miner Res.* 11: 1043–1051, 1996). Further, discontinuation of estrogen has been reported to lead to an increase in IL-6 secretion by murine bone marrow and bone cells (Girasole et al., *J. Clin. Invest.* 89:883–891, 1992; Jilka et al., *Science* 257:88–91, 1992; Kimble et al., *Endocrinology* 136:3054–3061, 1995; Passeri et al., *Endocrinology* 133:822–828, 1993), antibodies against IL-6 can inhibit the increase in osteoclast precursors occurring in estrogen-depleted mice (Girasole et al, supra), and bone loss following ovariectomy does not occur in transgenic mice lacking IL-6 (Poli et al., *EMBO J.* 13:1189–1196, 1994).

Existing treatments for slowing bone loss generally involves administration of compounds such as estrogen, bisphosphonates, calcitonin, and raloxifene. These compounds, however, are generally used for long-term treatments, and have undesirable side effects. Further, such treatments are typically directed to the activity of mature osteoclasts, rather than reducing their formation. For example, estrogen induces the apoptosis of osteoclasts, while calcitonin causes the osteoclasts to shrink and detach from the surface of the bone (Hughes et al., *Nat. Med.* 2:1132–1136, 1996; Jilka et al., *Exp. Hematol.* 23:500–506, 1995). Similarly, bisphosphonates decrease osteoclast activity, change their morphology, and increase the apoptosis of osteoclasts (Parfitt et al., *J. Bone Miner Res.* 11: 150–159, 1996; Suzuki et al., *Endocrinology* 137:4685–4690, 1996).

Cytokines are also believed to play an important role in a variety of cancers. For example, in the context of prostate cancer, researchers have shown IL-6 to be an autocrine/paracrine growth factor (Seigall et al., *Cancer Res.* 50:7786, 1999), to enhance survival of tumors (Okamoto et al., *Cancer Res.* 57:141–146, 1997), and that neutralizing IL-6 antibodies reduce cell proliferation (Okamoto et al., *Endocrinology* 138:5071–5073, 1997; Borsellino et al., *Proc. Annu. Meet. Am. Assoc. Cancer Res.* 37:A2801, 1996). Similar results have been reported for IL-6 with regard to multiple myeloma (Martinez-Maza et al., *Res. Immunol.* 143:764–769, 1992; Kawano et al., *Blood* 73:517–526, 1989; Zhang et al., *Blood* 74:11–13, 1989; Garrett et al., *Bone* 20:515–520, 1997; and Klein et al., *Blood* 78:1198–12–4, 1991), renal cell carcinoma (Koo et al., *Cancer Immunol.* 35:97–105, 1992; Tsukamoto et al., *J. Urol.* 148:1778–1782, 1992; and Weissglas et al., *Endocrinology* 138:1879–1885, 1997), and cervical carcinoma (Estuce et al., *Gynecol. Oncol.* 50:15–19, 1993; Tartour et al., *Cancer Res.* 54:6243–6248, 1994; and Iglesias et al., *Am. J. Pathology* 146:944–952, 1995).

Furthermore, IL-6 is also believed to be involved in arthritis, particularly in adjuvant-, collagen- and antigen-induced arthritis (Alonzi et al., *J. Exp. Med.* 187:146–148, 1998; Ohshima et al., *Proc. Natl. Acad. Sci. USA* 95:8222–8226, 1998; and Leisten et al., *Clin. Immunol. Immunopathol* 56:108–115, 1990), and anti-IL-6 antibodies have been reported for treatment of arthritis (Wendling et al., *J. Rheumatol.* 20:259–262, 1993). In addition, estrogen has been shown to induce suppression of experimental autoimmune encephalomyelitis and collagen-induced arthritis in mice (Jansson et al., *Neuroimmunol.* 53:203–207, 1994)

The cytokine IL-6 has also been shown to be an important factor in inducing the formation of osteoclasts (Girasole et al., supra; Jilka et al. (1992), supra; Jilka et al. (1995), supra; Kimble et al. (1995), supra; Pacifici et al., supra; and Passeri et al., supra). Other investigators have shown that administration of the neutralizing antibody, antisense oligos, or the Sant 5 antagonist against IL-6, reduces the number of osteoclasts in trabecular bone of ovariectomized mice (Devlin et al., *J. Bone Miner* 13:393–399, 1998; Girasole et al., supra; Jilka et al. (1992), supra, and Schiller et al., *Endocrinology* 138:4567–4571, 1997), the ability of human giant cells to resorb dentine (Ohsaki et al., *Endocrinology* 131:2229–2234, 1993; and Reddy et al., *J. Bone Min. Res.* 9:753–757, 1994), and the formation of osteoclasts in normal human bone marrow culture. It has also been found that estrogen downregulates the IL-6 promoter activity by interactions between the estrogen receptor and the transcription factors NF-κB and C/EBPβ (Stein et al., *Mol. Cell Biol.* 15:4971–4979, 1995).

Granulocyte-macrophage colony-stimulating factor (GM-CSF) has been suggested to play a role in the proliferation of osteoclastic precursor cells. In long term cultures of human or mouse bone marrow cells or peripheral blood cells, GM-CSF promotes the formation of osteoclastic cells (Kurihara et al., *Blood* 74:1295–1302, 1989; Lorenzo et al., *J. Clin. Invest.* 80:160–164, 1987; MacDonald et al., *J. Bone Miner* 1:227–233, 1986; and Shinar et al, *Endocrinology* 126:1728–1735, 1990). Bone marrow cells isolated from postmenopausal women, or women who discontinued estrogen therapy, expressed higher levels of GM-CSF than cells from premenopausal women (Bismar et al., *J. Clin. Endocrinol. Metab.* 80:3351–3355, 1995). Expression of GM-CSF has also been shown to be associated with the tissue distribution of bone-resorbing osteoclasts in patients with erosion of orthopedic implants (Al-Saffar et al., *Anatomic Pathology* 105:628–693, 1996).

As noted above, it had previously been assumed that estrogen binds to a single estrogen receptor (ER) in cells, causing conformational changes that result in release from heat shock proteins and binding of the receptor as a dimer to the so-called estrogen response element in the promoter region of a variety of genes. Further, pharmacologists have generally believed that non-steroidal small molecule ligands compete for binding of estrogen to ER, acting as either antagonists or agonists in each tissue where the estrogen receptor is expressed. Thus, such ligands have traditionally been classified as either pure antagonists or agonists. This is no longer believed to be correct.

Rather, it is now known that estrogen modulates cellular pharmacology through gene expression, and that the estrogen effect is mediated by estrogen receptors. As noted above, there are currently two estrogen receptors, ER-α and ER-β. The effect of estrogen receptor on gene regulation can be mediated by a direct binding of ER to the estrogen response element (ERE)—"classical pathway" (Jeltsch et al., *Nucleic Acids Res.* 15:1401–1414, 1987; Bodine et al., *Endocrinology* 139:2048–2057, 1998), binding of ER to other transcription factors such as NF-κB, C/EBP-β or AP-1—"non-classical pathway" (Stein et al., *Mol. Cell Biol.* 15:4971–4979, 1995; Paech et al., *Science* 277:1508–1510, 1997; Duan et al., *Endocrinology* 139:1981–1990, 1998), and through non-genomic effects via extranuclear estrogen receptor signaling that potentially include plasma membrane ER (Nadal, A. et al., *Trends in Pharmacological Sciences* 22:597–599, 2001; Wyckoff, M. H. et al., *J. Biol. Chem.* 276: 27071–27076, 2001; Chung, Y-L. et al., *Int. J. of Cancer* 97:306–312, 2002; Kelly, M. J. et al., *Trends Endocrinol. Metab.* 10:369–374, 1999; Levin, E. R. et al., *Trends Endocrinol. Metab.* 10:374–377, 1999).

Progress over the last few years has shown that ER associates with co-activators (e.g., SRC-I, CBP and SRA) and co-repressors (e.g., SMRT and N-CoR), which also modulate the transcriptional activity of ER in a tissue-specific and ligand-specific manner. In such cases, ER interacts with the transcription factors critical for regulation of these genes. Transcription factors known to be modulated in their activity by ER include, for example, AP-1, NF-κB, C/EBP and Sp-1. In addition, orphan nuclear receptors, such as estrogen receptor-related receptors α, β, γ (ERR-α, ERR-β, ERR-γ), have been identified. Although estradiol does not appear to be a ligand for the ERRs, some SERMs and other traditional ER-ligands have been shown to bind to the receptors with high affinity (Coward, P. et al., *Proc. Natl Acad. Sci.* 98:8880–8884, 2001; Lu, D. et al., *Cancer Res.* 61:6755–6761, 2001; Tremablay, G. B. et al., *Endocrinology* 142:4572–4575, 2001; Chen, S. et al., *J. Biol. Chem.* 276:28465–28470, 2001).

Furthermore, ER-α and ER-β have both overlapping and different tissue distributions, as analyzed predominantly by RT-PCR or in-situ hybridization due to a lack of good ER-β antibodies. Some of these results, however, are controversial, which may be attributable to the method used for measuring ER, the species analyzed (rat, mouse, human) and/or the differentiation state of isolated primary cells. Very often tissues express both ER-α and ER-β, but the receptors are localized in different cell types. In addition, some tissues (such as kidney) contain exclusively ER-α, while other tissues (such as uterus, pituitary and epidymis) show a great predominance of ER-α (Couse et al., *Endocrinology* 138, 4613–4621, 1997; Kuiper et al., *Endocrinology* 138, 863–870, 1997). In contrast, tissues expressing high levels of ER-β include prostate, testis, ovaries and certain areas of the brain (Brandenberger et al., *J. Clin. Endocrinol. Metab.* 83, 1025–8, 1998; Enmark et al., *J. Clinic. Endocrinol. Metabol.* 82, 4258–4265, 1997; Laflamme et al., *J. Neurobiol.* 36, 357–78, 1998; Sar and Welsch, *Endocrinology* 140, 963–71, 1999; Shughrue et al., *Endocrinology* 138, 5649–52, 1997a; Shughrue et al., *J. Comp. Neurol.* 388, 507–25, 1997b).

The development of ER-α (Korach, *Science* 266, 1524–1527, 1994) and ER-β (Krege et al., *Proc. Natl. Acad. Sci. USA* 95, 15677–82, 1998) knockout mice further demonstrate that ER-β has different functions in different tissues. For example, ER-α knockout mice (male and female) are infertile, females do not display sexual receptivity and males do not have typical male-aggressive behavior (Cooke et al., *Biol. Reprod.* 59, 470–5, 1998; Das et al., *Proc. Natl. Acad. Sci. USA* 94, 12786–12791, 1997; Korach, 1994; Ogawa et al., *Proc. Natl. Acad. Sci. USA* 94, 1476–81, 1997; Rissman et al., *Endocrinology* 138, 507–10, 1997a; Rissman et al., *Horm. Behav.* 31, 232–243, 1997b). Further, the brains of these animals still respond to estrogen in a pattern that is similar to that of wild-type animals (Shughrue et al., *Proc. Natl. Acad. Sci. USA* 94, 11008–12, 1997c), and estrogen still inhibits vascular injury caused by mechanical damage (Iafrati et al., *Nature Med.* 3, 545–8, 1997). In contrast, mice lacking the ER-β develop normally, are fertile and exhibit normal sexual behavior, but have fewer and smaller litters than wild-type mice (Krege et al., 1998), have normal breast development and lactate normally. The reduction in fertility is believed to be the result of reduced ovarian efficiency, and ER-β is the predominant form of ER in the ovary, being localized in the granulosa cells of maturing follicles.

In summary, compounds which serve as estrogen antagonists or agonists have long been recognized for their significant pharmaceutical utility in the treatment of a wide variety of estrogen-related conditions, including conditions related to the brain, bone, cardiovascular system, skin, hair follicles, immune system, bladder and prostate (Barkhem et al., *Mol. Pharmacol.* 54, 105–12, 1998; Farhat et al., *FASEB J.* 10, 615–624, 1996; Gustafsson, *Chem. Biol.* 2, 508–11, 1998; Sun et al., 1999; Tremblay et al., *Endocrinology* 139, 111–118, 1998; Turner et al., *Endocrinology* 139, 3712–20, 1998). In addition, a variety of breast and non-breast cancer cells have been described to express ER, and serve as the target tissue for specific estrogen antagonists (Brandenberger et al., 1998; Clinton and Hua, *Crit. Rev. Oncol. Hematol.* 25, 1–9, 1997; Hata et al., *Oncology* 55 Suppl 1, 35–44, 1998; Rohlff et al., *Prostate* 37, 51–9, 1998; Simpson et al., *J Steroid Biochem Mol Biol* 64, 137–45, 1998; Yamashita et al., *Oncology* 55 Suppl 1,17–22, 1998).

In recent years a number of both steroidal and nonsteroidal compounds which interact with ER have been developed. For example, Tamoxifen was originally developed as an anti-estrogen and used for the treatment of breast cancer, but more recently has been found to act as a partial estrogen agonist in the uterus, bone and cardiovascular system. Raloxifene is another compound that has been proposed as a SERM, and has been approved for treatment of osteoporosis.

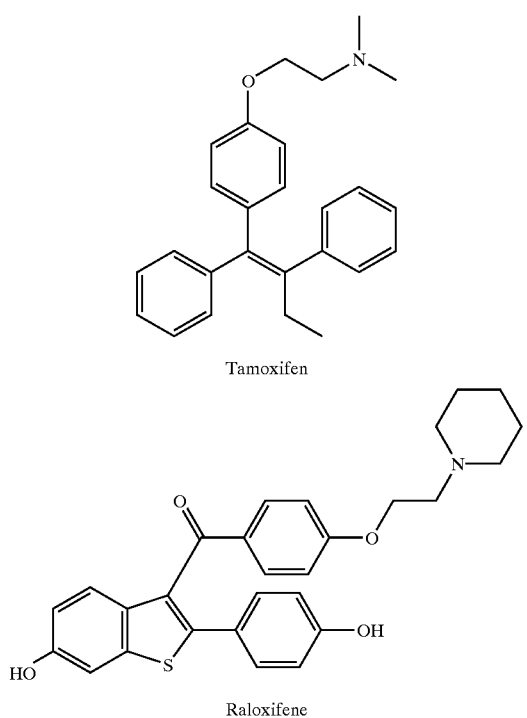

Analogs of Raloxifene have also been reported (Grese et al., *J. Med. Chem.* 40:146–167, 1997).

As for coumarin-based compounds, a number of structures have been proposed, including the following: Roa et al., *Synthesis* 887–888, 1981; Buu-Hoi et al., *J. Org. Chem.* 19:1548–1552, 1954; Gupta et al., *Indian J. Exp. Biol.* 23:638–640, 1985; Published PCT Application No. WO 96/31206; Verma et al., *Indian J. Chem.* 32B:239–243, 1993; Lednicer et al., *J. Med. Chem.* 8:725–726, 1965; Micheli et al., *Steroids* 5:321–335, 1962; Brandt et al., *Int. J. Quantum Chemistry: Quantum Biol. Symposia* 13:155–165, 1986; Wani et al., *J. Med. Chem.* 18:982–985, 1975; Pollard et al., *Steroids* 11:897–907, 1968.

Accordingly, there is a need in the art for compounds useful for treating a bone-resorbing disease, cancer, arthritis or an estrogen-related condition.

Citation or identification of any reference in Section 2 of this application is not to be construed as an admission that the reference is prior art to the present application.

SUMMARY OF THE INVENTION

The invention relates to compounds having the following general structure (1):

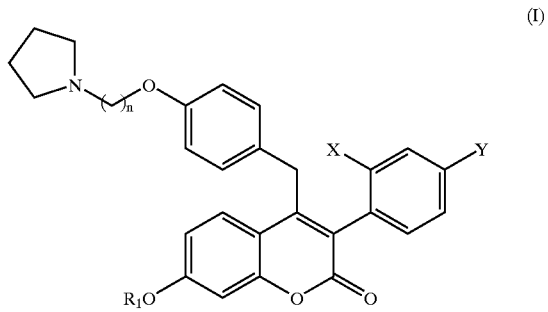

and pharmaceutically acceptable salts thereof, wherein:

n is 2, 3 or 4;

$R_1$ is hydrogen, $C(=O)R_2$, $C(=O)OR_2$, $C(=O)NHR_2$, $C(=O)NR_2R_3$, or $S(=O_2)NR_2R_3$;

$R_2$ and $R_3$ are independently $C_{1-8}$alkyl, $C_{6-12}$aryl, $C_{7-12}$arylalkyl, or a five- or six-membered heterocycle containing up to two heteroatoms selected from O, $NR_4$ and $S(O)_q$, wherein each of the above groups are optionally substituted with one to three substituents independently selected from $R_5$ and q is 0, 1 or 2;

$R_4$ is hydrogen or $C_{1-4}$alkyl;

$R_5$ is hydrogen, halogen, hydroxy, $C_{1-6}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$aryl, $C_{7-12}$aralkyl, COOH, CN, $CONHOR_6$, $SO_2NHR_6$, $NH_2$, $C_{1-4}$alkylamino, $C_{1-4}$dialkylamino, $NHSO_2R_6$, $NO_2$, or a five- or six-membered heterocycle, where each occurrence of $R_6$ is independently $C_{1-6}$alkyl;

X is hydrogen, halogen or trifluoromethyl; and

Y is halogen or trifluoromethyl.

The invention also relates to a method of obtaining a compound of formula (I), wherein $R_1$ is H, by demethylation of a compound of formula (II).

The invention further relates to a method for inhibiting a cytokine in a patient, comprising administering to a patient in need thereof an effective amount of a compound of formula (I), or a pharmaceutically acceptable salt of the compound.

The invention further relates to a method for treating or preventing a bone-resorbing disease in a patient, comprising administering to a patient in need thereof an effective amount of a compound of formula (I), or a pharmaceutically acceptable salt of the compound.

The invention further relates to a method for treating or preventing cancer in a patient, comprising administering to a patient in need thereof an effective amount of a compound of formula (I), or a pharmaceutically acceptable salt of the compound.

The invention further relates to a method for treating or preventing arthritis in a patient, comprising administering to a patient in need thereof an effective amount of a compound of formula (I), or a pharmaceutically acceptable salt of the compound.

The invention further relates to a method for modulating gene expression in a cell expressing ER, comprising contacting the cell with an effective amount of a compound of formula (I), or a pharmaceutically acceptable salt of the compound.

The invention further relates to a method for modulating gene expression in a tissue expressing ER, comprising contacting the cell with an effective amount of a compound of formula (I), or a pharmaceutically acceptable salt of the compound.

The invention further relates to a method for treating or preventing an estrogen related condition in a patient, comprising administering to a patient in need thereof an effective amount of a compound of formula (I), or a pharmaceutically acceptable salt of the compound.

The present invention may be understood more fully by reference to the detailed description and examples, which are intended to exemplify non-limiting embodiments of the invention.

DETAILED DESCRIPTION OF THE INVENTION

The invention relates to compounds of formula (I):

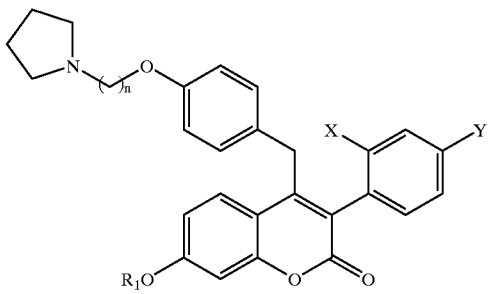

(I)

and pharmaceutically acceptable salts thereof, wherein:

n is 2, 3 or 4;

$R_1$ is hydrogen, $C(=O)R_2$, $C(=O)OR_2$, $C(=O)NHR_2$, $C(=O)NR_2R_3$, or $S(=O_2)NR_2R_3$;

$R_2$ and $R_3$ are independently $C_{1-8}$alkyl, $C_{6-12}$aryl, $C_{7-12}$arylalkyl, or a five- or six-membered heterocycle containing up to two heteroatoms selected from O, $NR_4$ and $S(O)_q$, wherein each of the above groups are optionally substituted with one to three substituents independently selected from $R_5$ and q is 0, 1 or 2;

$R_4$ is hydrogen or $C_{1-4}$alkyl;

$R_5$ is hydrogen, halogen, hydroxy, $C_{1-6}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$aryl, $C_{7-12}$aralkyl, COOH, CN, $C(=O)NHOR_6$, $S(=O_2)NHR_6$, $NH_2$, $C_{1-4}$alkylamino, $C_{1-4}$dialkylamino, $NHSO_2R_6$, $NO_2$, or a five- or six-membered heterocycle, where each occurrence of $R_6$ is independently $C_{1-6}$alkyl;

X is hydrogen, halogen or trifluoromethyl; and

Y is halogen or trifluoromethyl.

In a preferred embodiment, the compounds of formula (I) are those wherein n=2 and $R_1$ is hydrogen.

The invention further relates to a method for obtaining compounds of formula (I), wherein $R_1$ is H, comprising the step of demethylating a compound of formula (II) shown below:

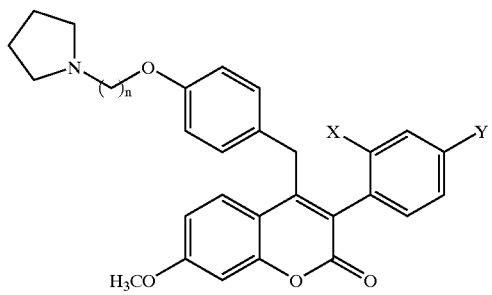

(II)

or a pharmaceutically acceptable salt thereof, wherein n is 2, 3 or 4 and X and Y are as defined above.

The demethylation of compounds of formula (II) can be achieved using any method known in the art useful in the deprotection of phenolic methyl ethers. Examples of such methods can be found in Greene, T. W., *Protective Groups in Organic Synthesis*, Chapter 3, John Wiley and Sons, New York, 1981, pp. 88–92, which is incorporated herein by reference in its entirety. Preferably, demethylation proceeds by a method comprising contacting a compound of formula (II) with about 1.0 to about 50.0 molar equivalents of a demethylating agent such as iodotrimethylsilane, pyridine hydrochloride, hydrobromic acid, hydrochloric acid, hydroiodic acid, a Grignard reagent, a Lewis acid or a strong nucleophile. More preferably, the demethylating agent is aqueous HBR, more preferably as a mixture in acetic acid. In a more preferred embodiment, demethylation is achieved by heating the compound of formula (II), or a pharmaceutically acceptable salt thereof, in the presence of the demethylating agent, optionally in the presence of a solvent, preferably a carboxylic acid, at a temperature of about room temperature to about 200° C., preferably at a temperature of about 100° C. to about 160° C. for 15 minutes to about 24 hours. In one embodiment, the demethylation reaction vessel is sealed, for example a sealed tube, to prevent solvent evaporation, particularly where the boiling point of the solvent is lower than the temperature of the demethylation reaction. The acid salt of compounds of formula (I), wherein $R_1$ is H, can be obtained by isolating the compound directly from the demethylation reaction which can then be used to prepare the corresponding pharmaceutically acceptable salt. The free base form is available upon washing the acid salt with an appropriate base such as sodium hydroxide and isolating the compound.

The resulting compounds of formula (I), wherein $R_1$ is H, that are produced by demethylation of compounds of formula (II), are useful as cytokine inhibitors as well as for the treatment or prevention of a bone-resorbing disease, cancer, arthritis or an estrogen-related condition. The compounds of formula (I), wherein $R_1$ is H, that are produced by demethylation of compounds of formula (II) are also useful as intermediates in the synthesis of compounds of formula (I) wherein $R_1$ is $C(=O)R_2$, $C(=O)OR_2$, $C(=O)NHR_2$, $C(=O)NR_2R_3$, or $S(=O_2)NR_2R_3$.

The compounds of formula (I) and pharmaceutically acceptable salts thereof (collectively, the "benzopyranone compounds"), are useful for treating or preventing a bone-resorbing disease, cancer, arthritis or an estrogen-related condition. The benzopyranone compounds are also useful for inhibiting a cytokine in a patient and modulating gene expression in a cell and/or tissue expressing ER. Thus, the compounds of this invention may be administered as a therapeutic and/or prophylactic agent.

As used herein, a "$C_{6-12}$aryl" is an aromatic moiety containing from 6 to 12 carbon atoms. In one embodiment, the $C_{6-12}$aryl is selected from (but not limited to) phenyl, tetralinyl, and napthalenyl.

A "$C_{7-12}$aralkyl" is an arene containing from 7 to 12 carbon atoms, and has both aliphatic and aromatic units. In one embodiment, the $C_{7-12}$aralkyl is an aryl group bonded directly through an alkyl group, such as (but not limited to) benzyl, ethylbenzyl (i.e., —(CH$_2$)$_2$phenyl), propylbenzyl and isobutylbenzyl.

A "$C_{3-12}$heterocycle" is a compound that contains a ring made up of more than one kind of atom, and which contains 3 to 12 carbon atoms, including (but not limited to) pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl.

A "$C_{4-16}$heterocyclealkyl" is a compound that contains a $C_{3-12}$heterocycle as listed above linked to a $C_{1-8}$alkyl.

A "$C_{1-8}$alkyl" is a straight chain or branched carbon chain containing from 1 to 8 carbon atoms, including (but not limited to) methyl, ethyl, n-propyl, n-butyl, n-pentyl, n-hexyl, and the like. Similarly, a "$C_{1-x}$alkyl has the same meaning, but wherein "x" represents the number of carbon atoms less than eight, such as $C_{1-6}$alkyl.

A "substituted" $C_{1-x}$alkyl, $C_{6-12}$aryl, $C_{7-12}$aralkyl, $C_{3-12}$heterocycle, or $C_{4-16}$heterocyclealkyl moiety is a $C_{1-x}$alkyl, $C_{6-12}$aryl, $C_{7-12}$aralkyl, $C_{3-12}$heterocycle, or $C_{4-16}$heterocyclealkyl moiety having at least one hydrogen atom replaced with a substituent.

A "substituent" is a moiety selected from halogen, —OH, —R', —OR', —COOH, —COOR', —COR', —CONH$_2$, —NH$_2$, —NHR', —NR'R', —SH, —SR', —SOOR', —SOOH and —SOR', where each occurrence of R' is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl.

A "halogen" is fluorine, chlorine, bromine or iodine.

The benzopyranone compounds can have chiral centers and can occur as racemates, racemic mixtures and as individual enantiomers or diastereomers. All such isomeric forms are included within the present invention, including mixtures thereof. Furthermore, some of the crystalline forms of the benzopyranone compounds can exist as polymorphs, which are included in the present invention. In addition, some of the benzopyranone compounds can also form solvates with water or other organic solvents. Such solvates are similarly included within the scope of this invention.

An estrogen "agonist" is a compound that binds to ER and mimics the action of estrogen in one or more tissues, while an "antagonist" binds to ER and blocks the action of estrogen in one or more tissues. Further, the term "estrogen-related condition" encompasses any condition associated with elevated or depressed levels of estrogen, a selective estrogen receptor modulator (SERM) or ER. In this context, ER includes both ER-α and/or ER-β, as well as any isoforms, mutations and proteins with significant homology to ER.

A "patient" is an animal, including, but not limited to, an animal such a cow, monkey, horse, sheep, pig, chicken, turkey, quail, cat, dog, mouse, rat, rabbit, and guinea pig, and is more preferably a mammal, and most, preferably a human.

Although not intending to be limited by the following theory, particularly in the context of bone-resorbing diseases, it is believed that the benzopyranone compounds function by blocking cytokine production and/or by inhibiting formation of osteoclasts.

The present invention also relates to pharmaceutical compositions comprising an effective amount of a benzopyranone compound and optionally a pharmaceutically acceptable carrier or vehicle, wherein a pharmaceutically acceptable carrier or vehicle can comprise an excipient, diluent, or a mixture thereof. Other embodiments of the present invention include methods for treating or preventing bone-resorbing diseases, including, but not limited to, osteoporosis, metastatic bone cancer and hypercalcemia, osteolytic lesions with orthopedic implants, Paget's disease, and bone loss associated with hyperparathyroidism; conditions associated with IL-6, including various cancers and arthritis; cancer, including breast cancer, prostrate cancer, colon cancer, endometrial cancer, multiple myeloma, renal cell carcinoma and cervical carcinoma; and arthritis, including adjuvant-, collagen-, bacterial- and antigen-induced arthritis, particularly rheumatoid arthritis. These methods comprise administering an effective amount of a benzopyranone compound to a patient in need thereof.

In addition, the benzopyranone compounds are useful for treating or preventing a wide range of estrogen-related conditions, including, but not limited to, breast cancer, osteoporosis, endometriosis, cardiovascular disease, hypercholesterolemia, prostatic hypertrophy, prostatic carcinomas, obesity, hot flashes, skin effects, mood swings, memory loss, prostate cancer, menopausal syndromes, hair loss (alopecia), type-II diabetes, Alzheimer's disease, urinary incontinence, GI tract conditions, spermatogenesis, vascular protection after injury, endometriosis, learning and memory, CNS effects, plasma lipid levels, acne, cataracts, hirsutism, other solid cancers (such as colon, lung, ovarian, melanoma, CNS, and renal), multiple myeloma, lymphoma, and adverse reproductive effects associated with exposure to environmental chemicals or natural hormonal imbalances.

The benzopyranone compounds are also useful for oral contraception; relief for the symptoms of menopause; prevention of threatened or habitual abortion; relief of dysmenorrhea; relief of dysfunctional uterine bleeding; relief of endometriosis; an aid in ovarian development; treatment of acne; diminution of excessive growth of body hair in women (hirsutism); the prevention or treatment of cardiovascular disease; prevention and treatment of atherosclerosis; prevention and treatment of osteoporosis; treatment of benign prostatic hyperplasia and prostatic carcinoma obesity; and suppression of post-partum lactation. The benzopyranone compounds also have a beneficial effect on plasma lipid levels and as such are useful in treating and preventing hypercholesterolemia. The benzopyranone compounds are further useful in the treatment and prevention of breast and ovarian cancer.

In another embodiment, the invention relates to a method for inhibiting a cytokine in a patient, comprising administering to a patient in need thereof an effective amount of a compound of formula (I), (II) or a pharmaceutically acceptable salt of the compound.

In a further embodiment, the invention relates to a method for modulating gene expression in a cell expressing ER, comprising contacting the cell with an effective amount of a compound of formula (I), (II) or a pharmaceutically acceptable salt of the compound.

In a further embodiment, the invention relates to a method for modulating gene expression in a tissue expressing ER, comprising contacting the cell with an effective amount of a compound of formula (I), (II) or a pharmaceutically acceptable salt of the compound.

The benzopyranone compounds can be prepared according to the general reaction schemes (Route 1 and Route 2) shown below.

Route 1:
STEP 1.

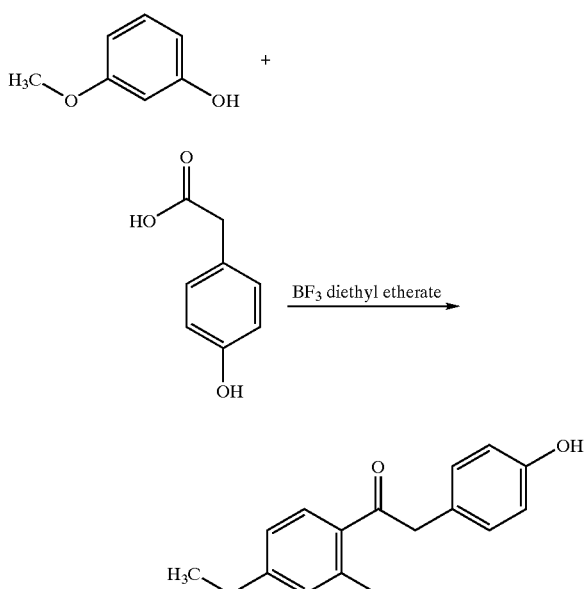

STEP 2.

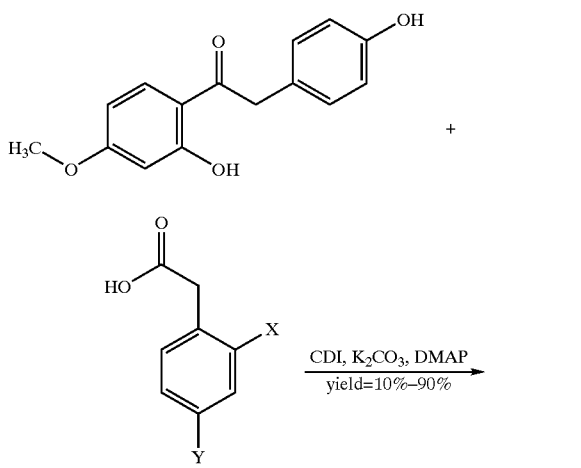

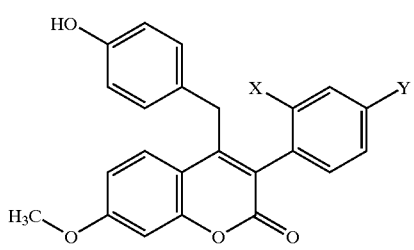

-continued
STEP 3.

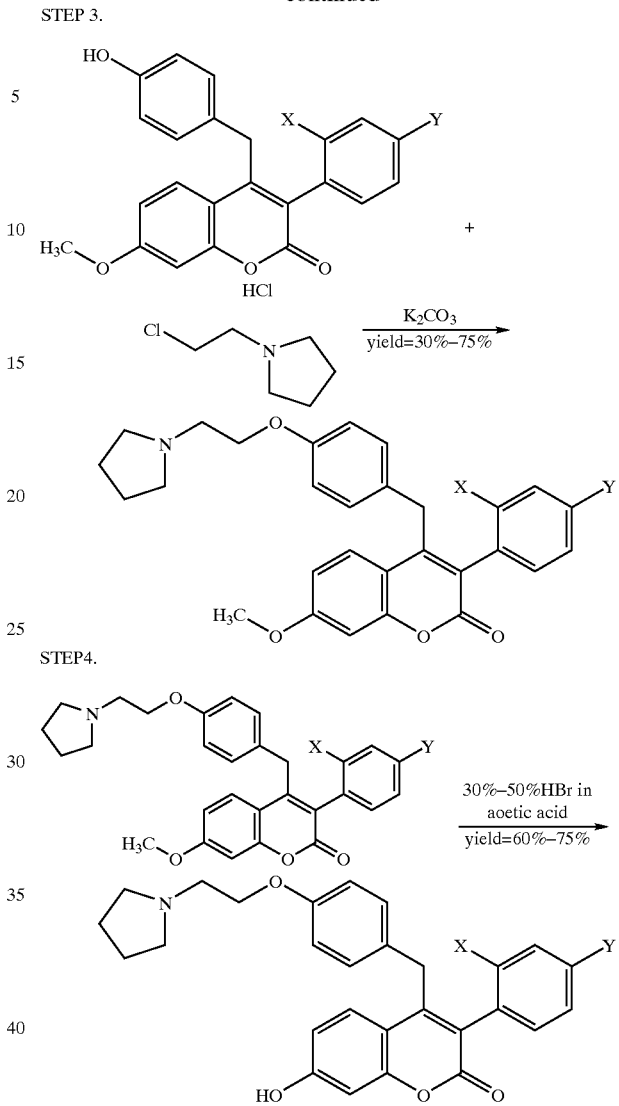

Step 1: Fries Reaction
Reaction yields are 40% to 55% and the reaction has been run on gram to multiple kilogram scale. On smaller scale reactions POCl$_3$ (solvent) and ZnCl$_2$ have been used in place of the BF$_3$ diethyl etherate.

Step 2: Coumarin Formation Reaction Summary
Reaction yields are typically 10% to 90% and the reactions have been run on a multiple gram scale. Powdered K$_2$CO$_3$ is essential for efficient reaction. Reactions have also been run by adding all reagents simultaneously instead of preactivating the acid as described above. Under these conditions slightly lower yields are obtained.

Step 3: Side-chain Introduction Reaction Summary
Reaction yields are typically 30% to 70% and the reactions have been run on multiple gram scale. Powdered K$_2$CO$_3$ is essential and granular material results in incomplete or prolonged reaction times. The reaction yield in the examples provided are our most recent efforts and the yields were lower than expected. In the case of the dichloro analog, product precipitated on the column during flash chromatography In general this is the highest yielding step of the reaction sequence. The side-chain has also been introduced as described in the alternative synthesis scheme.

Step 4: Demethylation Reaction Summary

Reaction yields are typically 60% to 75%. Sealed tube reaction minimizes HBr escape and greatly facilitates the reaction rate. Reactions run at atmospheric pressure require one day or more for completion.

Route 2:

STEP 1.

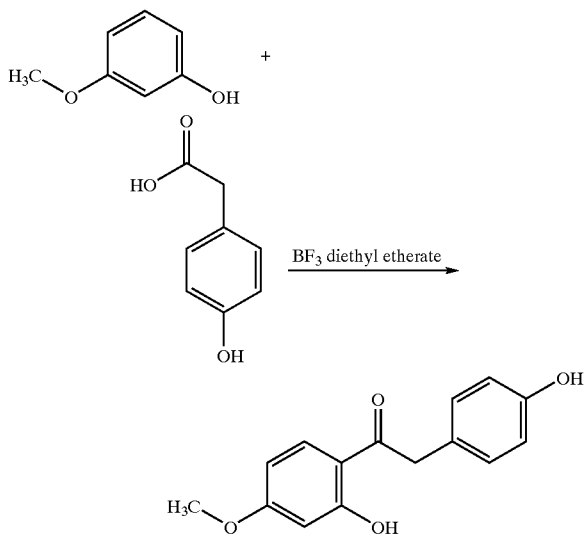

STEP 2.

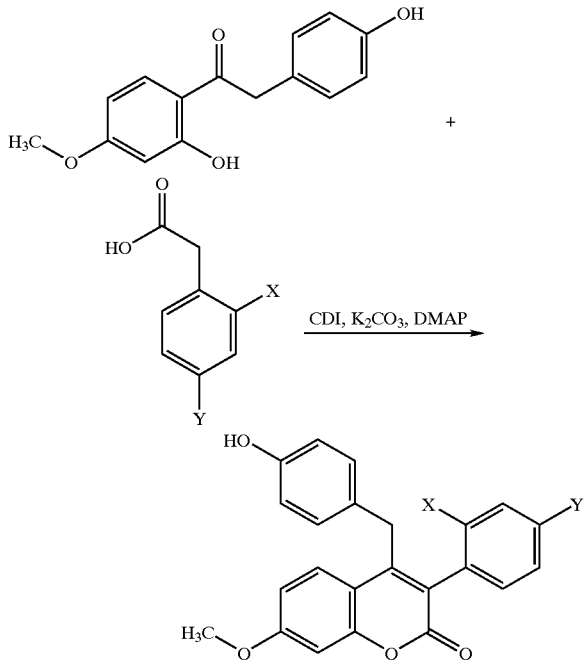

STEP 3.

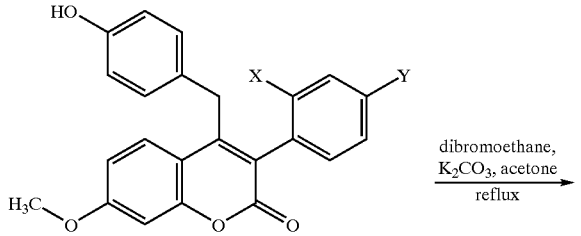

-continued

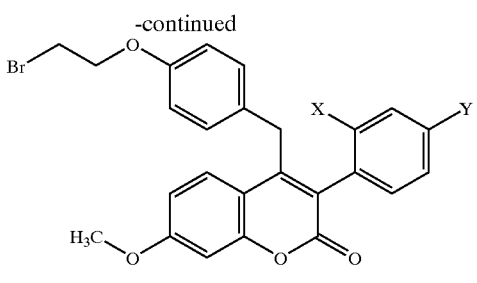

STEP 4.

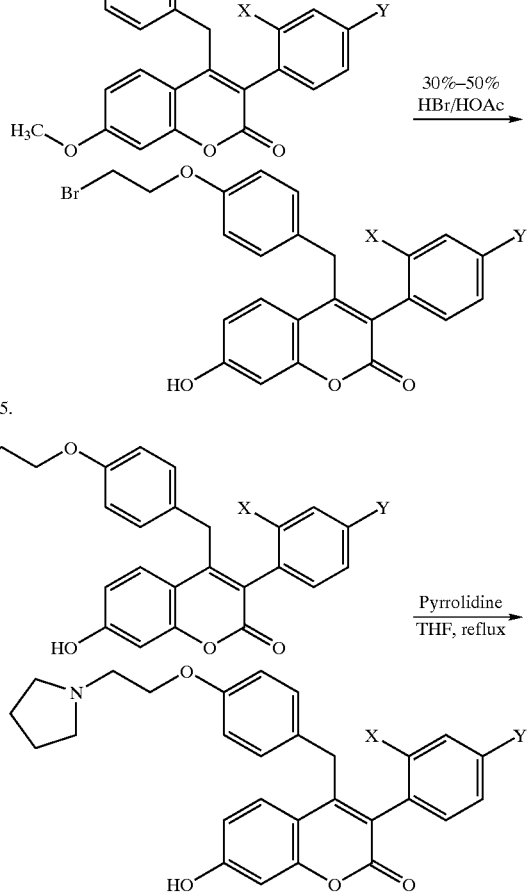

Methods of this invention involve administering an effective amount of a benzopyranone compound, or a pharmaceutical composition containing one or more of the same, to a patient in need thereof in an amount sufficient to treat the disease or condition of interest. To that end, the term "treat" (or the related terms "treating" and "treatment") means administration of a compound, typically in combination with an appropriate delivery vehicle or agent, to a patient that does not show signs of a disease or condition (e.g., prophylactic or preventative administration) or that does show signs of a disease or condition (e.g., curative or treatment administration). Further, the phrase "effective amount" means a benzopyranone compound dose that, after a given time, results in the desired effect. For example, in the context of bone-resorbing disease, an effective amount results in bones mass that is statistically different from that of animals treated with placebo. Similarly, for cancer and arthritis, an effective amount is an amount sufficient to produce the desired effect on the cancerous or arthritic tissue.

The benzopyranone compounds can exist as a pharmaceutically acceptable salt of a compound of structure (I) or (II). The pharmaceutically acceptable acid addition salts of the benzopyranone compounds can be formed of the compound itself, or of any of its esters, and include the pharmaceutically acceptable salts which are often used in pharmaceutical chemistry. For example, salts may be formed with organic or inorganic acids. Suitable organic acids include maleic, fumaric, benzoic, ascorbic, succinic, methanesulfonic, benzenesulfonic, toluenesulfonic, acetic, oxalic, trifluoroacetic, propionic, tartaric, salicylic, citric, gluconic, lactic, mandelic, cinnamic, aspartic, stearic, palmitic, formic, glycolic, glutamic, and benzenesulfonic acids. Suitable inorganic acids include hydrochloric, hydrobromic, sulfuric, phosphoric, and nitric acids. Additional salts include chloride, bromide, iodide, bisulfate, acid phosphate, isonicotinate, lactate, acid citrate, oleate, tannate, pantothenate, bitartrate, gentisinate, gluconate, glucaronate, saccharate, ethanesulfonate, p-toluenesulfonate, and pamoate (i.e., 1,1'-methylene-bis-(2-hydroxy-3-naphthoate)) salts. The term "pharmaceutically acceptable salt" is intended to encompass any and all acceptable salt forms.

Pharmaceutically acceptable salts can be formed by conventional and known techniques, such as by reacting a compound of this invention with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the benzopyranone compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

The benzopyranone compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g, water), and base wax (e.g., cocoa butter, white petrolatum or polyethylene glycol). The effective amount of the benzopyranone compound in the pharmaceutical composition may be at a level that will exercise the desired effect; for example, about 0.1 mg to 100 mg in unit dosage for both oral and parenteral administration.

The benzopyranone compound can be usually administered one to four times a day with a unit dosage of 0.1 mg to 100 mg in human patients, but the above dosage may be properly varied depending on the age, body weight and medical condition of the patient and the type of administration. A preferred dose is 0.25 mg to 25 mg in human patients. One dose per day is preferred.

The dose of a benzopyranone compound to be administered to a human is rather widely variable and subject to the judgment of the attending physician. It should be noted that it may be necessary to adjust the dose of a benzopyranone compound when it is administered in the form of a salt, such as a laureate, the salt forming moiety of which has an appreciable molecular weight. The general range of effective administration rates of the benzopyranone compounds is from about 0.05 mg/day to about 100 mg/day. A preferred rate range is from about 0.25 mg/day to 25 mg/day. Of course, it is often practical to administer the daily dose of a benzopyranone compound in portions, at various hours of the day. However, in any given case, the amount of benzopyranone compound administered will depend on such factors as the solubility of the active component, the formulation used and the route of administration.

It is usually preferred to administer a benzopyranone compound orally for reasons of convenience. However, the benzopyranone compounds may equally effectively be administered percutaneously, or as suppositories for absorption by the rectum, if desired in a given instance.

The benzopyranone compounds can be administered as pharmaceutical compositions. The compositions can be in the form of tablets, chewable tablets, capsules, solutions, parenteral solutions, troches, suppositories and suspensions. Compositions can be formulated to contain a daily dose, or a convenient fraction of a daily dose, in a dosage unit, which may be a single tablet or capsule or convenient volume of a liquid.

The compositions can be readily formulated as tablets, capsules and the like; it is preferable to prepare solutions from water-soluble salts, such as the hydrochloride salt. In general, all of the compositions are prepared according to known methods in pharmaceutical chemistry. Capsules are prepared by mixing the benzopyranone compound with a suitable diluent and filling the proper amount of the mixture in capsules. The usual diluents include inert powdered substances such as starch of many different kinds, powdered cellulose, especially crystalline and microcrystalline cellulose sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a benzopyranone compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the benzopyranone compounds can be delayed or prolonged by proper formulation. For example, a slowly soluble pellet of the benzopyranone compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the benzopyranone compound in oily or emulsified vehicles that allow it to disperse slowly in the serum.

EXAMPLES

The following Examples are presented by way of illustration, not limitation.

Example 1

3-(2-Chloro-4-trifluoromethylphenyl)-7-hydroxy-4-(4-(2-pyrrolidin-1-yl-ethoxy)-benzyl)-chromen-2-one A. (2-Chloro-4-trifluoromethylphenyl)-acetic acid

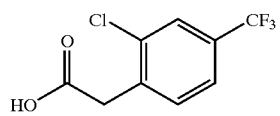

A solution of LiHMDS in toluene was prepared by the addition of n-BuLi (357 mL of a 1.6 M solution in hexanes, 571 mmol) to a cold (−78° C.) solution of HMDS (120.5 mL, 571 mmol) in toluene (700 mL). After 30 min, the reaction mixture was allowed to warm up to 10° C. over 1 h. The solution was then transferred via a cannula to a flame-dried, three-neck flask under $N_2$ containing $Pd_2dba_3$ (4.18 g, 4.57 mmol) and (2'-dicyclohexylphosphanylbiphenyl-2-yl)-dimethylamine (3.77 g, 9.59 mmol). The mixture was stirred for 15 min at 15° C., cooled to −10° C. and t-butylacetate (70.5 mL, 525.4 mmol) was added dropwise. After 10 min, 3-chloro-4-iodobenzotrifluoride (70 g, 228.4 mmol) was added and the reaction mixture was warmed up to 28° C. After stirring at this temperature for 1.5 h, the mixture was filtered through silica gel, using toluene as eluent, and the solvent was removed in vacuo. The residue was purified using flash chromatography (silica gel, 98:2 hexanes:EtOAc) to yield (2-chloro-4-trifluoromethylphenyl)-acetic acid tert-butyl ester as a solid.

A solution of (2-chloro-4-trifluoromethylphenyl)-acetic acid tert-butyl ester (40 g, 135.7 mmol) in dioxane (100 mL) containing conc. HCl (31.3 mL) was stirred at 50° C. for 5 h. After cooling the mixture to r.t., it was diluted with $Et_2O$ and the organic layer was washed with $H_2O$ (3×). The organic phase was dried ($MgSO_4$) and the solvent was removed in vacuo. Recrystallization of the residue with AcOEt-hexane yielded the title compound as a solid showing: $^1$H NMR (400 MHz, $CDCl_3$) δ 7.71 (s, 1H), 7.55 (dd, 1H, J=1.0, 8.0 Hz), 7.47 (d, 1H, J=8.0 Hz), 3.92 (s, 2H). MS (ESI) m/z 237 (M−H)$^-$.

B. 3-(2-Chloro-4-trifluoromethylphenyl)-4-(4-hydroxy-benzyl)-7-methoxy-chromen-2-one

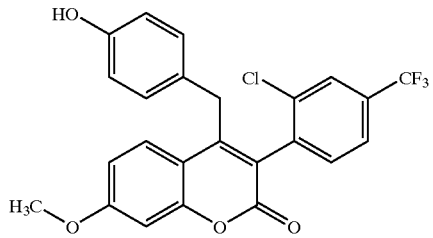

A mixture of 2-(chloro-4-trifluoromethylphenyl)-acetic acid (3.2 g, 13.41 mmol) and 1,1'-carbonyldiimidazole (2.72 g, 16.77 mmol) in DMF (15 mL) was heated to 70° C. for 25 min. The reaction mixture was cooled to 10° C. and $K_2CO_3$ (2.78 g, 20.1 mmol), 1-(2-hydroxy-4-methoxyphenyl)-2-(4-hydroxyphenyl)-ethan-1-one (1.73 g, 6.7 mmol, prepared as described in Example 4A), DMAP (164 mg, 1.34 mmol) and DMF (10 mL) were added. After stirring the reaction mixture at 115° C. for 1.5 h, the resulting suspension was cooled to r.t., poured onto AcOEt/$H_2O$ and the layers were separated. The organic layer was washed with $H_2O$, aq 1N HCl and brine, was dried ($MgSO_4$) and the solvent was removed in vacuo. The resultant red residue was purified using flash chromatography (silica gel, 2:1 to 1:2 hexanes:$Et_2O$) to provide the title compound as a white solid showing: $^1$H NMR (300 MHz, $CDCl_3$) δ 7.75 (s, 1H), 7.53 (br d, 1H, J=8.0 Hz), 7.47 (d, 1H, J=9.0 Hz), 7.33 (d, 1H, J=8.0 Hz), 6.92–6.85 (m, 3H), 6.80 (d, 1H, J=2.5, 9.0 Hz), 6.70 (d, 2H), J=8.5 Hz), 4.95–4.64 (very br s, 1H), 4.02 (d, 1H, J=15.5 Hz), 3.88 (s, 3H), 3.76 (d, 1H, J=15.5 Hz). MS (ESI) m/z 461 (M+H)$^+$.

C. 3-(2-Chloro-4-trifluoromethylphenyl)-7-methoxy-4-(4-(2-pyrrolidin-1-yl-ethoxy)-benzyl)-chromen-2-one

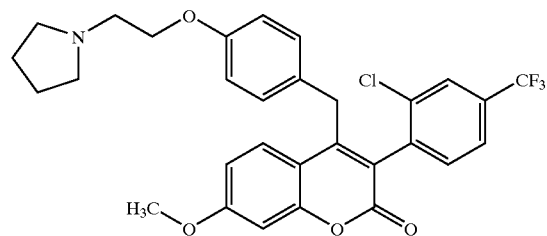

A mixture of 3-(2-chloro-4-trifluoromethylphenyl)-4-(4-hydroxybenzyl)-7-methoxychromen-2-one (460 mg, 1 mmol), 1-(2-chloroethyl)pyrrolidine hydrochloride (254.7 mg, 1.5 mmol) and $K_2CO_3$ (413.9 mg, 2.99 mmol) in EtOH (5 mL) was stirred for 2 min prior to the addition of $H_2O$ (0.5 mL). The mixture was stirred at 55° C. for 2.5 h, after which time it was cooled to r.t. and poured into $CHCl_3$—$H_2O$. The layers were separated and the aqueous phase was extracted with $CHCl_3$ (3×). The combined organic layers were washed with brine, dried (MgSO$_4$) and the solvent was removed in vacuo. The resultant brown foam was purified using flash chromatography (silica gel, 19:1 CH$_2$Cl$_2$:MeOH) to provide the title compound as a pale brown foam which displayed: $^1$H NMR (300 MHz, CD$_3$OD) δ 7.83 (s, 1H), 7.65 (d, 1H, J=9.0 Hz), 7.63 (d, 1H, J=8.0 Hz), 7.51 (d, 1H, J=8.0 Hz), 7.00 (d, 1H, J=2.5 Hz), 6.95 (d, 2H, J=8.5 Hz), 6.89 (dd, 1H, J=2.5, 9.0 Hz), 6.79 (d, 2H, J=8.5 Hz),), 4.07 (d, 1H, J=15.5 Hz), 4.05 (t, 2H, J=5.5 Hz), 3.90 (s, 3H), 3.83 (d, 1H, J=15.5 Hz), 2.89 (t, 2H, J=5.5 Hz), 2.72–2.60 (m, 4H), 1.90–1.75 (m, 4H). MS (ESI) m/z 558 (M+H)$^+$.

D. 3-(2-Chloro-4-trifluoromethylphenyl)-7-hydroxy-4-(4-(2-pyrrolidin-1-yl-ethoxy)-benzyl)-chromen-2-one

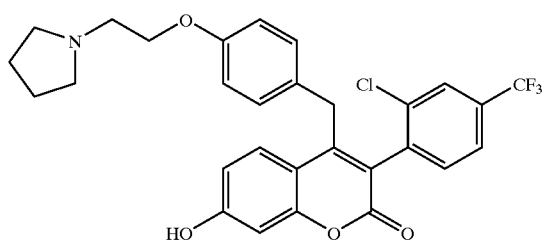

3-(2-Chloro-4-trifluoromethylphenyl)-7-methoxy-4-(4-(2-pyrrolidin-1-yl-ethoxy)-benzyl)-chromen-2-one (330 mg, 0.59 mmol) was dissolved in AcOH (2.4 mL)-48% aq HBr (2.4 mL). The mixture was stirred at 130° C. for 15 h. After cooling the mixture to r.t., it was poured onto EtOAc/aq NaHCO$_3$. 1M aq NaOH was then added to bring the pH to 8. The layers were separated and the aqueous layer was back-extracted with EtOAc (3×). The combined organic layers were washed with brine, dried (MgSO$_4$) and the solvent was removed in vacuo. The residue was purified using flash chromatography (silica gel, 5:1 CH$_2$Cl$_2$-MeOH) to provide the title compound as a yellow foam showing: IR (KBr) v=3670–2140, 1709, 1611, 1569, 1511, 1367, 1323, 1247, 1172, 1133, 1081, 1067, 1044, 1012 cm$^{-1}$. $^1$H NMR (400 MHz, CD$_3$OD) δ 7.81 (d, 1H, J=1.5 Hz), 7.61 (dd, 1H, J=1.5, 8.0 Hz), 7.56 (d, 1H, J=8.8 Hz), 7.48 (d, 1H, J=8.0 Hz), 6.93 (d, 2H, J=8.5 Hz), 6.79 (d, 2H), J=8.5 Hz), 6.76 (d, 1H, J=2.5 Hz), 6.73 (dd, 1H, J=2.5, 8.8 Hz), 4.09 (t, 2H, J=5.5 Hz), 4.05 (d, 1H, J=15.5 Hz), 3.80 (d, 1H, J=15.5 Hz), 3.04 (t, 2H, J=5.5 Hz), 2.86–2.78 (m, 4H), 1.92–1.82 (m, 4H). HRMS (ESI) calcd for C$_{29}$H$_{25}$ClF$_3$NO$_4$ (M+H)$^+$: 544.1502; found 544.1504.

Example 2

3-(2-Chloro-4-trifluoromethylphenyl)-7-hydroxy-4-(4-(2-pyrrolidin-1-yl-ethoxy)-benzyl)-chromen-2-one A. (4-Chloro-2-trifluoromethylphenyl)-acetic acid

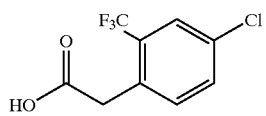

A solution containing 4-chloro-1-iodo-2-trifluoromethylbenzene (14.98 g, 48.9 mmol), Bu$_3$SnCH=CH$_2$ (15.7 mL, 53.7 mmol) and (Ph$_3$P)$_4$Pd (2.26 g, 1.955 mmol) in anhyd toluene (200 mL) was deoxygenated using vacuum-N$_2$ flush (3×). After refluxing the reaction mixture for 17 h, it was cooled to 0° C. and a solution of disiamylborane-methyl sulfide complex in toluene (~1.95 M, 47 mL) was added dropwise over a period of ~5 min. The disiamylborane-methyl sulfide complex solution was prepared by adding 2-methyl-2-butene (26 mL, 245 mmol) to a cold (0° C.) solution of borane-methyl sulfide complex (11.6 mL, 122.3 mmol ) in anhyd toluene (25 mL) and stirring the resultant mixture at r.t. for 2 h. The bath was removed and the reaction mixture was stirred at r.t. for 3 h. After that period of time, the mixture was cooled to 0° C., EtOH (75 mL) was added slowly, followed by 2 N aq NaOH (37.5 mL) and 30% aq H$_2$O$_2$ (30 mL). The solution was stirred at r.t. for 1.5 h and was then poured onto Et$_2$O—H$_2$O. The layers were separated and the organic layer was washed with H$_2$O and brine, was dried (MgSO$_4$) and the solvent was removed in vacuo, while the bath temperature was maintained below 30° C. The black residue was purified using flash chromatography (silica gel; 4:1 to 3:1 hexanes:AcOEt) to afford 2-(4-chloro-2-trifluoromethyl-phenyl)-ethanol as a brown oil which was used directly in the next step.

To a solution of 2-(4-chloro-2-trifluoromethylphenyl)-ethanol in acetone (50 mL) at 0° C. was added dropwise a solution of Jones reagent (40.3 mL of a 2.67 M solution in H$_2$SO$_4$). After 25 min, the mixture was poured onto Et$_2$O/H$_2$O and the layers were separated. The organic layer was washed with H$_2$O and brine, dried (MgSO$_4$) and the solvent was removed in vacuo. The resultant orange solid was crystallized from hexane and heptane to furnish the title compound as a solid which showed: $^1$H NMR (300 MHz, CDCl$_3$) δ 7.67 (d, 1H, J=2.0Hz), 7.51 (dd, 1H, J=2.0, 8.0Hz), 7.34 (d, 1H, J=8.0Hz), 3.84 (s, 2H).

B. 3-(4-Chloro-2-trifluoromethylphenyl)-4-(4-hydroxybenzyl)-7-methoxy-chromen-2-one

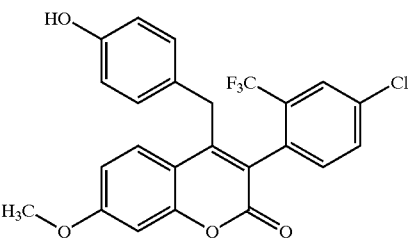

This compound was prepared using the methodology described above in Example 1B. The resultant residue was purified using flash chromatography (silica gel, 1:1 to 55:45 to 3:2 Et$_2$O:hexanes) to provide the title compound as a beige solid showing: $^1$H NMR (300 MHz, CDCl$_3$) δ 7.76 (d, 1H, J=1.5 Hz), 7.50 (dd, 1H, J=1.5, 8.0 Hz), 7.41 (d, 1H, J=9.0 Hz), 7.15 (d, 1H, J=8.0 Hz), 6.89 (d, 1H, J=2.5 Hz), 6.85 (d, 2H, J=8.5 Hz), 6.77 (dd, 1H, J=2.5, 9.0 Hz), 6.70 (d, 2H, J=8.5 Hz), 4.00 (d, 1H, J=15.5 Hz), 3.87 (s, 3H), 3.61 (d, 1H, J=15.5 Hz). MS (ESI) m/z 461 (M+H)$^+$.

C. 3(4-Chloro-2-trifluoromethylphenyl)-7-methoxy-4-(4-(2-pyrrolidin-1-yl-ethoxy)-benzyl)-chromen-2-one

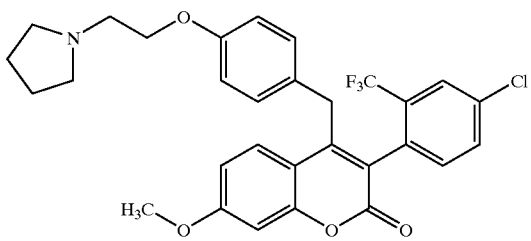

This compound was prepared using the methodology described above in Example 1C. The resultant brown foam was purified using flash chromatography (silica gel, 94:6 CH$_2$Cl$_2$:MeOH) to provide the title compound as a light yellow foam which displayed: $^1$H NMR (300 MHz, CD$_3$OD) δ 7.83 (d, 1H, J=1.7 Hz), 7.61 (dd, 1H, J=1.7, 8.5 Hz), 7.55 (d, 1H, J=9.0 Hz), 7.34 (d, 1H, J=8.5 Hz), 7.00–6.93 (m, 3H), 6.85 (dd, 1H, J=2.5, 9.0 Hz), 6.81 (d, 2H, J=9.0 Hz), 4.11 (d, 1H,J=15.5 Hz), 4.05 (t, 2H, J=5.5 Hz), 3.88 (s, 3H), 3.61 (d, 1H, J=15.5 Hz), 2.90 (t, 2H, J=5.5 Hz), 2.71–2.61 (m, 4H), 1.8–1.77 (m, 4H). MS (ESI) m/z 558 (M+H)$^+$.

D. 3(4-Chloro-2-trifluoromethylphenyl)-7-hydroxy-4-(4-(2-pyrrolidin-1-yl-ethoxy)-benzyl)-chromen-2-one

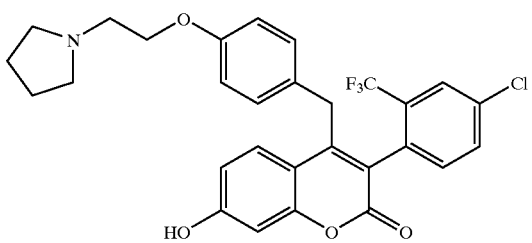

This compound was prepared using the methodology described above in Example 1D. The residue was purified using flash chromatography (silica gel, 5:1 CH$_2$Cl$_2$-MeOH) to provide the title compound as a yellow solid showing: IR (KBr) ν=3700–2100, 1721, 1597, 1512, 1467, 1377, 1305, 1265, 1247, 1182, 1136, 1108, 1061, 1046, 1016, 843cm-1. $^1$H NMR (400 MHz, CD$_3$OD) δ 7.82 (d, 1H, J=2.0 Hz), 7.59 (dd, 1H, J=2.0, 8.0 Hz), 7.47 (d, 1H, J=9.0Hz), 7.31 (d, 1H, J=8.0 Hz), 6.96 (d, 2H, J=8.5 Hz), 6.82 (d, 2H, J=8.5 Hz), 6.75 (d, 1H, J=2.5 Hz), 6.69 (dd, 1H, J=2.5, 9.0 Hz), 4.12–4.06 (m, 3H), 3.59 (d, 1H, J=15.5 Hz), 3.05 (t, 2H, J=5.5 Hz), 2.86–2.81 (m, 4H), 1.92–1.84 (m, 4H). HRMS (ESI) calcd for C$_{29}$H$_{25}$ClF$_3$NO$_4$ (M+H)$^+$: 544.1502; found: 544.1505.

Example 3

3-(2,4-bis-Trifluoromethylphenyl)-7-hydroxy-4-(4-(2-pyrrolidin-1-yl-ethoxy)-benzyl)-chromen-2-one A. 3-(2,4-bistrifluoroemethylphenyl)-4-(4-hydroxybenzyl)-7-methoxychromen-2-one

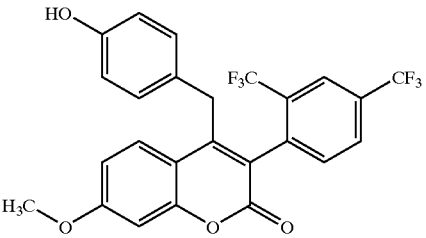

This compound was prepared using the methodology described above in Example 1B. The resultant residue was purified using flash chromatography (silica gel, 1:1 to 3 2 Et$_2$O:hexanes) to provide the title compound as a yellow foam showing: $^1$H NMR (300 MHz, CDCl$_3$) δ 8.03 (s, 1H), 7.78 (d, 1H, J=8.0 Hz), 7.42 (d, 1H, J=8.8 Hz), 7.36 (d, 1H, J=8.0 Hz), 6.90 (d, 1H, J=2.5 Hz), 6.84 (d, 2H, J=8.5 Hz), 6.78 (dd, 1H, J=2.5, 8.8 Hz), 6.70 (d, 2H, J=8.5 Hz), 4.76 (s, 1H), 4.01 (d, 1H, J=16.0 Hz), 3.88 (s, 3H), 3.57 (d, 1H, J=16.0Hz).

B. 3-(2,4-bistrifluoromethylphenyl)-7-methoxy-4-(2-pyrrolidin-1-yl-ethoxy)-benzyl)-chromen-2-one

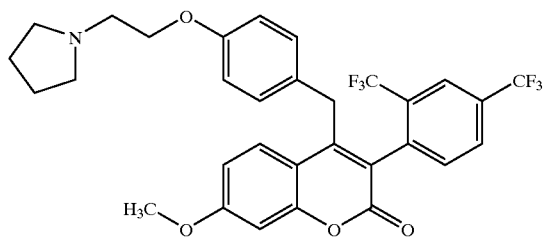

This compound was prepared using the methodology described above in Example 1C. The resultant brown foam was purified using flash chromatography (silica gel, 96:4 CH$_2$Cl$_2$:MeOH) to provide the title compound as a beige foam which displayed: $^1$H NMR (300 MHz, CD$_3$OD) δ 8.09 (s, 1H), 7.93 (d, 1H, J=8.5 Hz), 7.59 (d, 1H, J=8.5 Hz), 7.57 (d, 1H, J=9.0 Hz), 6.99 (d, 1H, J=2.5 Hz), 6.97 (d, 2H, J=8.5 Hz), 6.87 (dd, 1H, J=2.5, 9.0 Hz), 6.81 (d, 2H, J=8.5 Hz), 4.13 (d, 1H, J=16.0 Hz), 4.05 (t, 2H, J=5.5 Hz), 3.89 (s, 3H), 3.59 (d, 1H, J=16.0 Hz), 2.89 (t, 2H, J=5.5 Hz), 2.73–2.58 (m, 4H), 1.87–1.77 (m, 4H). MS (ESI) m/z 592 (M+H)$^+$.

C. 3-(2,4-bistrifluoromethylphenyl)-7-hydroxy-4-(4-(2-pyrrolidin-1-ylethoxy)-benzyl)-chromen-2-one

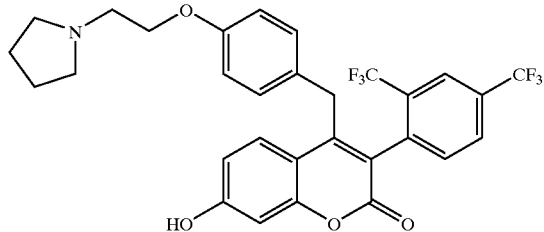

This compound was prepared using the methodology described above in Example 1D. The residue was purified using flash chromatography (silica gel, 3:1 CH$_2$Cl$_2$-MeOH) to provide the title compound as a yellow foam showing: IR (KBr) ν=3700–2300, 1714, 1615, 1512, 1462, 1368, 1346, 1300, 1272, 1179, 1133, 1082, 1062, 1045, 1014, 846 cm$^{-1}$. $^1$H NMR (400 MHz, CD$_3$OD) δ 8.07 (s, 1H), 7.91 (br d, 1H, J=8.5 Hz), 7.56 (d, 1H, J=8.5 Hz), 7.49 (d, 1H, J=8.8 Hz), 6.96 (d, 2H, J=9.0 Hz), 6.82 (d, 2H, J=9.0 Hz), 6.77 (d, 1H, J=2.5 Hz), 6.71 (dd, 1H, J=2.5, 8.8 Hz), 4.11 (d, 1H, J=16.0 Hz), 4.11 (t, 2H, J=5.5 Hz), 3.57 (d, 1H, J=16.0 Hz), 3.08 (t, 2H, J=5.5 Hz), 2.90–2.83 (m, 4H), 1.92–1.86 (m, 4H). HRMS (ESI) calcd for C$_{30}$H$_{25}$F$_6$NO$_4$ (M+H)$^+$: 578.1766; found: 578.1762.

Example 4

3-(4-Trifluromethylphenyl)-4-(4-(2-Pyrrolidin-1-yl-ethoxy)benzyl)-7-methoxychromen-2-one A. 1-(2-hydroxy-4-methoxyphenyl)-2-(4-hydroxyphenyl)ethan-1-one

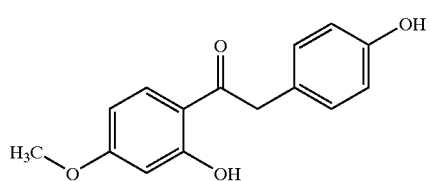

A suspension of 3-methoxyphenol (44.69 kg, 360 mol) and 4-hydroxyphenylacetic acid (68.5 kg, 450 mol) in 144 L of chlorobenzene was purged with nitrogen gas. Boron trifluoride diethyl etherate (177 L, 1440 mol) was added at 20 to 25° C. The suspension was heated to 80° C. and stirred for 4 to 5 h then cooled to 5 to 10° C. and stirred overnight.

The precipitated red/orange solid (undesired isomer) was filtered with N$_2$ pressure and the filtrate was quenched by pouring onto ice/H$_2$O. The filter cake was washed with CH$_2$Cl$_2$. The boron trifluoride etherate was quenched by the slow addition of 80% Na$_2$CO$_3$ (aq) until the pH of the aqueous solution reached 6 to 7. Gas evolution was observed and the product precipitated from solution.

The orange suspension was stirred at 20° C. overnight and subsequently filtered. The filter cake was washed with H$_2$O and MTBE and dried overnight to provide the desired product (38 kg, 42% yield, HPLC purity 95.1% a/a). $^1$H NMR (300 MHz, DMSO-d6) δ 12.30 (s, 1H), 9.31 (s, 1H), 7.99 (d, 1H, J=9.1 Hz), 7.08 (d, 2H, J=8.4 Hz), 6.70, (d, 2H, J=8.4 Hz), 6.53 (dd, 1H, J=2.5, 9.1 Hz), 6.47 (d, 1H, J=2.5 Hz), 4.18 (s, 2H), 3.81 (s, 3H). MS (ESI) m/z 259 (M+H)$^+$.

B. 3-(4-trifluoromethylphenyl)-4-(4-hydroxybenzyl)-7-methoxychromen-2-one

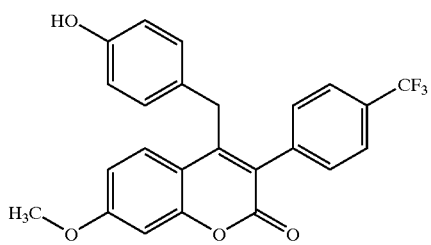

A solution of 4-trifluoromethylphenylacetic acid (15.2 g, 74.45 mmol) in 120 mL of DMF at 25° C. was treated with CDI (13.2 g, 82 mmol) in several portions over 5 minutes. The reaction mixture was warmed to 40° C. for 10 minutes then cooled to room temperature. 1-(2-hydroxy-4-methoxyphenyl)-2-(4-hydroxyphenyl)ethan-1-one (9.81 g, 38 mmol), K$_2$CO$_3$ (15.7 g, 114 mmol), and DMAP (0.93 g, 7.6 mmol) were added and the reaction mixture was warmed to 80° C. for 2 hours.

The suspension was cooled to room temperature and 200 mL of water was added. The aqueous layer was extracted with CH$_2$Cl$_2$ and the combined organic layer was dried (MgSO$_4$) then concentrated under vacuum. The resulting solid was purified using flash chromatography (CH$_2$Cl$_2$:EtOAc) to provide the desired product (10.2 g, 63%). $^1$H NMR (300 MHz, DMSO-d6) δ 9.29 (s, 1H), 7.79 (d, 2H, J=8.7 Hz), 7.57 (d, 2H, J=8.7 Hz), 7.53 (d, 1H, J=8.5 Hz), 7.04 (d, 1H, J=2.3 Hz), 6.93 (d, 2H, J=8.9 Hz), 6.87 (dd, 1H, J=8.5, 2.3 Hz), 6.61 (d, 2H, J=8.9 Hz), 3.90 (s, 2H), 3.84 (s, 3H). MS (ESI) m/z 427 (M+H)$^+$.

C. 3-(4-trifluoromethylphenyl)-4-(4-(2-pyrrolidin-1-ylethoxy)benzyl)-7-methoxychromen-2-one

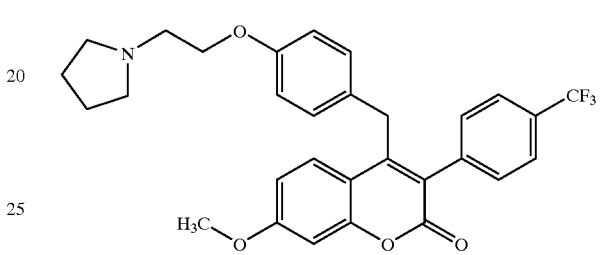

A solution of 3-(4-trifluoromethylphenyl)-4-(4-hydroxybenzyl)-7-methoxychromen-2-one (6.0 g, 14 mmol), 1-(2-chloroethyl)pyrrolidine hydrochloride (3.3 g, 22.5 mmol), and K$_2$CO$_3$ (6.6 g, 47.8 mmol) in 30 mL of DMF was warmed at 120° C. for 2 hours. Solvent was removed under reduced pressure. Water was added and the aqueous layer was extracted with ethyl acetate. The combined organic layer was dried and concentrated to provide a dark brown oil. Flash chromatography (CH$_2$Cl$_2$:EtOAc:MeOH:TEA) provided the desired product (4.7 grams, 64%). $^1$H NMR (300 MHz, DMSO-d6) δ 7.79 (d, 2H, J=8.1 Hz), 7.58 (d, 2H, J=8.1 Hz), 7.51 (d, 1H, J=9.0 Hz), 7.08 (d, 2H, J=8.9 Hz), 7.06 (d, 1H, J=2.5 Hz), 6.87 (dd, 1H, J=2.5, 9.0 Hz), 6.82 (d, 2H, J=8.9 Hz), 4.08 (t, 2H J=5.0 Hz), 3.96 (s, 2H), 3.84 (s, 3H), 3.17–3.12 (m, 2H), 2.94–2.88 (m, 4H), 1.8–1.78 (m, 4H). MS (ESI) m/z 524 (M+H)$^+$.

D. 3-(4-trifluoromethylphenyl)-4-(4-(2-pyrrolidin-1-yl-ethoxy)benzyl)-7-methoxychromen-2-one

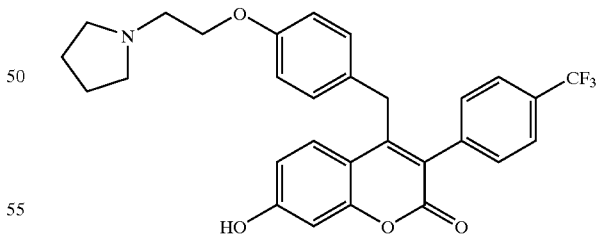

A solution of 3-(4-trifluoromethylphenyl)-4-(4-(2-pyrrolidin-1-yl-ethoxy)benzyl)-7-methoxychromen-2-one (4.2 grams, 8.02 mmol) and 25 mL of 30% HBr/HOAc in a sealed tube was warmed at 120° C. for 3 h. The solvent was removed under reduced pressure and the residue was quenched with NaHCO$_3$ (aq). The aqueous layer was extracted with CH$_2$Cl$_2$ and the combined organic layer was concentrated. The crude product was purified by passage through a short column of silica gel followed by reverse phase preparative HPLC to provide the title compound (2.9 g, 71%). $^1$H NMR (300 MHz, DMSO) δ 7.77 (d, 2H, J=8.0 Hz), 7.55 (d, 2H, J=8.0 Hz), 7.44 (d, 1H, J=8.8 Hz), 7.03 (d, 2H, J=8.0 Hz), 6.79 (d, 2H, 8.0 Hz), 6.76 (s, 1H), 6.70 (d, 1H, J=8.5 Hz), 3.97 (t, 2H, J=5.8 Hz), 3.92 (s, 2H), 2.72 (d, 2H, J=5.8 Hz), 2.50–2.47 (m, 4H), 1.66–1.64 (m, 4H). MS (ESI) m/z 510 (M+H)$^+$.

Example 5

3-(4-Chlorophenyl)-4-(4-(2-pyrrolidin-1-yl-ethoxy) benzyl)-7-hydroxychromen-2-one Hydrochloride A. 1-(2-hydroxy-4-methoxyphenyl)-2-(4-hydroxyphenyl) ethan-1-one

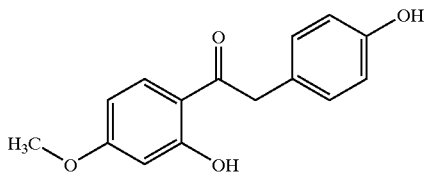

This compound was prepared using the methodology described above in Example 4A.

B. 3-(4-chlorophenyl)-4-(4-hydroxybenzyl)-7-methoxychromen-2-one

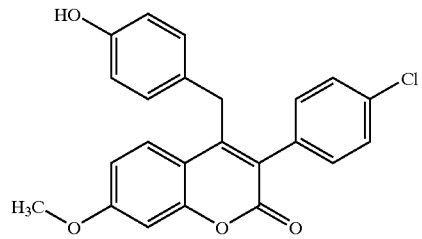

This compound was prepared using the methodology described above in Example 4B. $^1$H NMR (300 MHz, DMSO-d6) δ 9.30 (s, 1H), 7.51 (d, 1H, J=9.1 Hz), 7.47 (d, 2H, J=8.2 Hz), 7.34 (d, 2H, J=8.2 Hz), 7.02 (d, 1H, J=2.2 Hz), 6.91 (d, 2H, J=8.5 Hz), 6.85 (dd, 1H, J=9.1, 2.2 Hz), 6.61 (d, 2H, J=8.5 Hz), 3.91 (s, 2H), 3.83 (s, 3H). MS (ESI) m/z 393 (M+H)$^+$.

C. 3(4-chlorophenyl)-4-(4-(2-bromoethoxy)benzyl)-7-methoxychromen-2-one

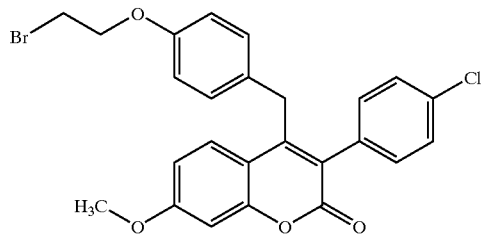

A solution of 3-(4-chlorophenyl)-4-(4-hydroxybenzyl)-7-methoxychromen-2-one (21.2 g, 54 mmol), dibromoethane (50.7 g, 270 mmol), and K$_2$CO$_3$ (8.3 g, 60 mmol) in 200 mL of acetone was heated at reflux for 12 h. The reaction mixture was cooled to room temperature and volatiles were removed under reduced pressure. Hexanes (500 mL) was added with stirring and the resulting solid that formed was collected by filtration. The material was rinsed with hexanes (2×100 mL), collected and dried under vacuum to provide the desired product (22.5 g, 83%). $^1$H NMR (300 MHz, DMSO) δ 7.50 (d, 1H, J=9.1 Hz), 7.48 (d, 2H, J=8.2 Hz), 7.35 (d, 2H, J=8.2 Hz), 7.07 (d, 2H, J=8.5 Hz), 7.04 (d, 1H, J=2.6 Hz), 6.86 (dd, 1H, J=9.1, 2.6Hz), 6.82 (d, 2H, J=8.5 Hz), 4.24 (t, 2H, J=5.8 Hz), 3.98 (s, 2H), 3.84 (s, 3H), 3.76 (t, 2H, J=5.8 Hz). MS (ESI) m/z 500 (M+H)$^+$.

D. 3(4-chlorophenyl)-4-(4-(2-bromoethoxy)benzyl)-7-hydroxychromen-2-one

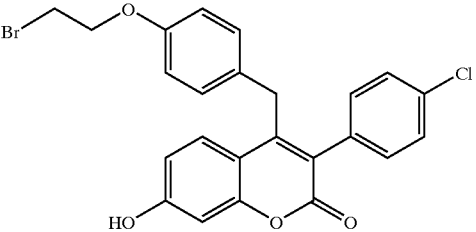

A solution of 3-(4-chlorophenyl)-4-(4-(2-bromoethoxy) benzyl)-7-methoxychromen-2-one (16.5 grams, 33 mmol) and 150 mL of 30% HBr/HOAc in a sealed tube was warmed at 100° C. for 8 h. The reaction mixture was cooled to room temperature and poured into 300 mL of water. The resulting solid was collected by filtration and purified using flash chromatography to provide the desired product (12.5 g, 78%). $^1$H NMR (300 MHz, DMSO) δ 10.55 (s, 1H), 7.47 (d, 2H, J=8.5 Hz), 7.43 (d, 1H, J=8.8 Hz), 7.33 (d, 2H, J=8.5 Hz), 7.05 (d, 2H, J=8.5 Hz), 6.83 (d, 2H, J=8.5 Hz), 6.75 (d, 1H, J=2.2 Hz), 6.70 (dd, 1H, J=8.8, 2.2 Hz), 4.24 (t, 2H, J=5.7 Hz), 3.94 (s, 2H), 3.76 (t, 2H, J=5.7 Hz). MS (ESI) m/z 486 (M+H)$^+$.

E. 3-(4-chlorophenyl)-4-(4-(2-pyrrolidin-1-ylethoxy) benzyl)-7-hydroxychromen-2-one hydrochloride

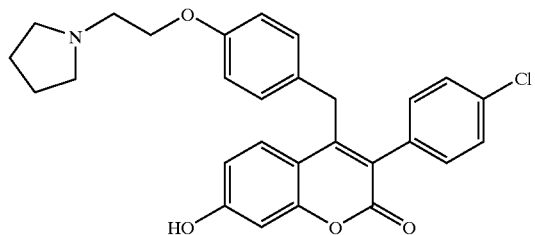

A solution of 3-(4-chlorophenyl)-4-(4-(2-bromoethoxy) benzyl)-7-hydroxychromen-2-one (8.3 g, 17.2 mmol) in 200 mL of THF was treated with 8 mL of pyrrolidine and the reaction mixture was heated at reflux for 5 h. The reaction mixture was concentrated and the crude product was purified using flash chromatography. The product was suspended in 250 mL of acetone and 4 mL of 5 M HCl(aq) was added. The mixture was stirred at room temperature overnight and the resulting solid was collected by filtration. The solid was suspended in 200 mL of ethyl acetate and the suspension was heated at reflux for 2h. The solution was cooled to room temperature and the final product was collected by filtration and dried under vacuum. The final yield was 4.96 grams (56%). $^1$H NMR (300 MHz, DMSO) δ 10.62 (s, 1H), 10.42 (s, 1H), 7.47 (d, 2H, J=8.5 Hz), 7.43 (d 1H, J=8.8 Hz), 7.34 (d, 2H, J=8.5 Hz), 7.09 (d, 2H, J=8.5 Hz), 6.87 (d, 2H, J=8.5 Hz), 6.77 (d, 1H, J=2.5 Hz), 6.71 (dd, 1H, J=2.5, 8.8 Hz), 4.26 (t, 2H, 4.9 Hz), 3.96 (s, 2H), 3.59–3.51 (m, 4H), 3.15–3.02 (m, 2H), 2.03–1.88 (m, 4H). MS (ESI) m/z 476 (M+H)$^+$.

Example 6

3-(2,4-Dichlorophenyl)-4-(4-(2-pyrrolidin-1-yl-ethoxy)benzyl)-7-hydroxychromen-2-one A. 1-(2-hydroxy-4-methoxyphenyl)-2-(4-hydroxyphenyl)ethan-1-one

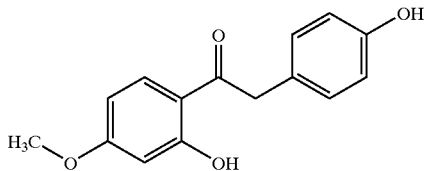

This compound was prepared using the methodology described above in Example 4A.

B. 3-(2,4-dichlorophenyl)-4-(4-hydroxybenzyl)-7-methoxychromen-2-one

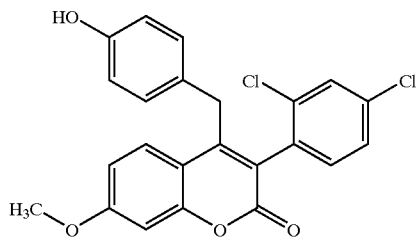

This compound was prepared using the methodology described above in Example 4B. 20 grams ketone (77.5 mmol) and 31.6 grams acid (155 mmol) provided 27.52 grams product (83%). $^1$H NMR (300 MHz, DMSO-d6) δ 9.26 (s, 1H), 7.5 8 (d, 1H, J=8.8 Hz), 7.50 (dd, 1H, J=1.9, 8.2 Hz), 7.45 (d, 1H, J=8.2 Hz), 7.06 (d, 1H, J=2.2 Hz), 6.90 (d, 3H, J=8.2 Hz), 6.59 (d, 2H, J=8.2 Hz), 3.98 (d, 1H, J=15.4 Hz), 3.85 (s, 3H), 3.69 (d, 1H, J=15.4 Hz). MS (ESI) m/z 428 (M+H)$^+$.

C. 3-(2,4-dichlorophenyl)-4-(4-(2-pyrrolidin-1-ylethoxy)benzyl)-7-methoxychromen-2-one

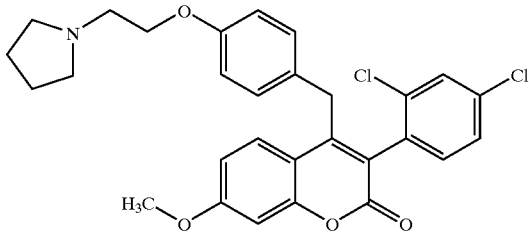

This compound was prepared using the methodology described above in Example 4C. (27.5 grams (64 mmol) of 3-(2,4-dichlorophenyl)-4-(4-hydroxybenzyl)-7-methoxychromen-2-one provided 13.5 grams product, 40% yield). $^1$H NMR (300 MHz, DMSO-d6) δ 7.75 (d, 1H, J=1.8 Hz), 7.57 (d, 1H, J=8.9 Hz), 7.51 (dd, 1H, J=1.8, 8.2 Hz), 7.47 (d, 1H, J=8.2 Hz), 7.07 (d, 1H, 2.5 Hz), 7.02 (d, 2H, J=8.7 Hz), 6.89 (dd, 1H, J=2.5, 8.9 Hz), 6.78 (d, 2H, J=8.7 Hz), 4.04 (d, 1H, J=15.4 Hz), 3.98 (t, 2H, J=5.8 Hz), 3.85 (s, 3H), 3.74 (d, 1H, J=15.4 Hz), 2.79 (t, 2H, J=5.8 Hz), 2.57–2.52 (m, 4H), 1.69–1.65 (m, 4H). MS (ESI) m/z 525 (M+H)$^+$.

D. 3-(2,4-dichlorophenyl)-4-(4-(2-pyrrolidin-1-yl-ethoxy)benzyl)-7-hydroxychromen-2-one

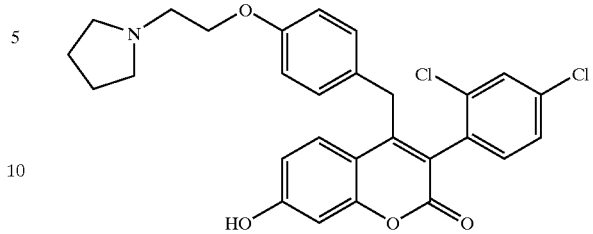

This compound was prepared using the methodology described above in Example 4D. (4.5 grams of 3-(2,4-dichlorophenyl)-4-(4-(2-pyrrolidin-1-ylethoxy)benzyl)-7-methoxychromen-2-one (8.5 mmol) provided 3.2 grams product, 73% yield). $^1$H NMR (300 MHz, CDCl$_3$) δ 7.49 (d, 1H, J=1.9 Hz), 7.35 (d, 1H, J=8.5 Hz), 7.27 (s, 1H) 7.23 (dd, 1H, J=2.2, 8.2 Hz), 7.04 (d, 1H, J=8.2 Hz), 6.81 (d, 2H, J=8.5 Hz), 6.67 (s, 1H), 6.65 (dd, 1H, J=2.2, 8.5 Hz), 6.56 (d, 2H, J=8.5 Hz), 3.99 (d, 1H, J=15.6 Hz), 3.97 (t, 2H, J=5.8 Hz), 3.71 (d, 1H, J=15.6 Hz), 2.73 (t, 2H, J=6.0 Hz), 2.51–2.46 (m, 4H), 1.68–1.63 (m, 4H). MS (ESI) m/z 511 (M+H)$^+$.

Example 7

Additional Representative Compounds

Table 1, below, discloses representative benzopyranone compounds. These benzopyranone compounds can be obtained using the methods disclosed herein.

TABLE 1

Representative Benzopyranone Compounds (I)

| No. | R$_1$ | X | Y | n |
|---|---|---|---|---|
| 1 | H | F | CF$_3$ | 2 |
| 2 | H | Br | CF$_3$ | 2 |
| 3 | H | I | CF$_3$ | 2 |
| 4 | C(=O)CH$_3$ | H | CF$_3$ | 2 |
| 5 | C(=O)CH$_3$ | Cl | CF$_3$ | 2 |
| 6 | C(=O)CH$_3$ | F | CF$_3$ | 2 |
| 7 | C(=O)CH$_3$ | Br | CF$_3$ | 2 |
| 8 | C(=O)CH$_3$ | I | CF$_3$ | 2 |
| 9 | C(=O)CH$_3$ | CF$_3$ | CF$_3$ | 2 |
| 10 | H | F | Cl | 2 |
| 11 | H | Br | Cl | 2 |
| 12 | H | I | Cl | 2 |
| 13 | C(=O)CH$_3$ | H | Cl | 2 |
| 14 | C(=O)CH$_3$ | Cl | Cl | 2 |
| 15 | C(=O)CH$_3$ | F | Cl | 2 |
| 16 | C(=O)CH$_3$ | Br | Cl | 2 |
| 17 | C(=O)CH$_3$ | I | Cl | 2 |
| 18 | C(=O)CH$_3$ | CF$_3$ | Cl | 2 |

Example 8

Inhibition of IL-6 Release

Illustrative benzopyranone compounds were tested for their ability to inhibit IL-6 release from human U-2 OS osteosarcoma cells stably transfected with human ER-α or ER-β. (Stein, B.; Yang, M. X. *Mol. Cell. Biol* 15: 4971–4979, 1995; Poli, V. et. al., *EMBO J.* 13:1189–1196, 1994). As a control, IL-6 release was determined from the parental non-transfected U-2 OS cell line, which does not express detectable levels of ER. Benzopyranone compounds having an $IC_{50}$<100 nM are particularly useful as bone resorption inhibitors in vivo. Accordingly, the compounds of this assay, illustrative benzopyranone compounds, are particularly useful for the treatment of osteoporosis, Paget's disease and metastatic bone cancer. These compounds are also useful as anti-cancer agents as elevated IL-6 levels are responsible for certain cancers such as multiple myeloma, prostate cancer, ovarian cancer, renal carcinoma and cervical carcinoma.

Human U-2 OS osteosarcoma cells (ATCC) were stably transfected with expression vectors for human full-length ER-α or ER-β, respectively, using standard molecular biology techniques. Stable subclones were generated that expressed high levels of ER-α or ER-β mRNA. The expression of ER-α and ER-β was confirmed using RNase protection analysis. The parental U-2 OS cells did not express any measurable amounts of either ER-α or ER-β.

Cells were plated into 96-well plates at a density of 80,000 cells per well in phenol red-free media with charcoal-stripped fetal calf serum. Twenty four hours later, cells were either treated with vehicle (0.2% DMSO) or test compound (0.01–1000 nm in 0.2% DMSO). Thirty minutes later cells were stimulated with 2.5 ng/ml TNFα and 1 ng/ml IL-1β. Twenty-four hours later the media supernatant was analyzed for cytokine production (IL-6) using commercially available ELISA kits following the manufacturer's instructions. Cytokine production in the presence of vehicle (0.2% DMSO) was set to 100%. The results are expressed as $IC_{50}$ (nM) values (Table 2) which is the concentration of the benzopyranone compound necessary to inhibit the production of IL-6 50% relative to the amount of IL-6 produced in the presence of vehicle. The results show that all of the illustrative benzopyranone compounds assayed show activity and, accordingly, are useful for treating or preventing bone-resorbing diseases such as osteoporosis, Paget's disease and metastatic bone cancer, and cancers such as multiple myeloma, prostate and ovarian cancer.

Example 9

Inhibition of MCF-7 Breast Cancer Cell Proliferation

This example shows the ability of illustrative benzopyranone compounds to inhibit 17β-estradiol-dependent growth of MCF-7 breast cancer cells in vitro and compares their activity to that of reference SERMs. MCF-7 cells represent an excellent in vitro system to study the effects of compounds on estrogen-dependent breast cancer growth. (May, F. E. B.; Westley, B. R. *J. Biol. Chem.* 262:15894–15899, 1987). Benzopyranone compounds having an $IC_{50}$<100 nM are particularly useful as anti-breast cancer agents in vivo.

MCF-7 breast carcinoma cells were plated in 24-well dishes at a density of $5\times10^3$ cells/well in phenol-red free DMEM:F-12 (1:1) medium containing 1% antibiotics, 0.05% mercaptoethanol, 0.01% ethanolamine, 0.42 ng/mL sodium selenite and 5% charcoal-stripped FCS.

Illustrative benzopyranone compounds (0.1–1000 nM in 0.2% DMSO) and 0.1 nM 17β-estradiol were added to the cultured MCF-7 breast cancer cells for 72 h. Subsequently, $^3$H-labeled thymidine was added and its incorporation into cells was measured following 4 h incubation. The results are expressed as $IC_{50}$ (nM) values (Table 2) which is the concentration of the benzopyranone compound necessary to inhibit the growth of MCF-7 breast cancer cells by 50% relative to controls. The results show that all the illustrative benzopyranone compounds assayed show activity and, accordingly, are useful for treating or preventing breast cancer in a patient.

Example 10

Inhibition of BG-1 Ovarian Carcinoma Cell Proliferation

This assay shows the ability of illustrative benzopyranone compounds to inhibit 17β-estradiol-dependent growth of BG-1 ovarian carcinoma cells in vitro and compares their ability to that of reference SERMs. BG-1 cells serve as a useful in vitro model for the evaluation of the effects of antiestrogenic compounds on ovarian tumor growth (Greenberger, L. M. et. al., *Clin. Cancer Res.* 7:3166–3177, 2001). Benzopyranone compounds having an $IC_{50}$<100 nM are particularly useful as anti-ovarian cancer agents in vivo.

BG-1 ovarian carcinoma cells were plated in 24-well dishes at a density of $5\times10^3$ cells/well in phenol-red free DMEM:F-12 (1:1) medium containing 1% antibiotics, 0.05% mercaptoethanol, 0.01% ethanolamine, 0.42 ng/mL sodium selenite and 5% charcoal-stripped FCS. Illustrative benzopyranone compounds (0.1–1000 nM in 0.2% DMSO) and 0.1 nM 17β-estradiol were added to the cultured BG-1 ovarian carcinoma cells and incubated for 72 h. Subsequently, $^3$H-labeled thymidine was added and its incorporation into cells was measured following 4h incubation. The results are expressed as $IC_{50}$ (nM) values (Table 2) which is the concentration of the benzopyranone compound necessary to inhibit the growth of BG-1 ovarian carcinoma cells by 50% relative to controls. The results show that all the illustrative benzopyranone compounds assayed show activity and, accordingly, are useful for treating or preventing ovarian cancer in a patient.

TABLE 2
In vitro data
| Structure | IC₅₀ (nM) | | |
|---|---|---|---|
| | IL-6 | MCF-7 | BG-1 |
| 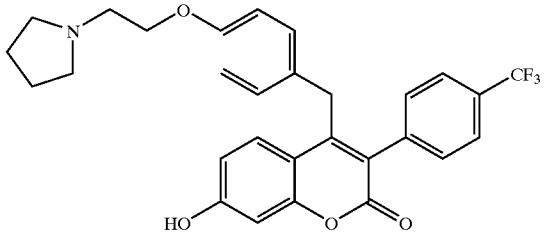 | 1.45 | 15.8 | 9.35 |
| 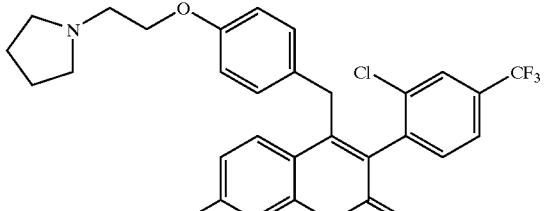 | 0.4 | 5.5 | 3.4 |
| 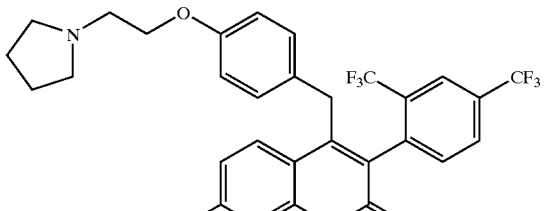 | 0.41 | 19 | 6.6 |
| 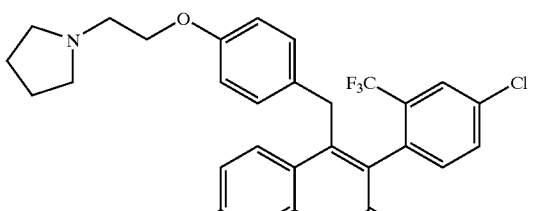 | 0.45 | 4.1 | 3.2 |
| 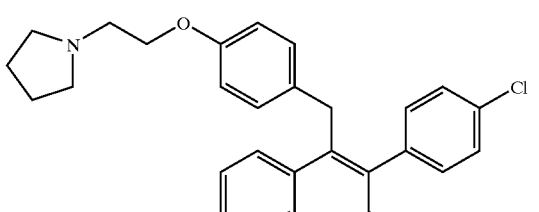 | 0.4 | 26.0 | 5.8 |
| 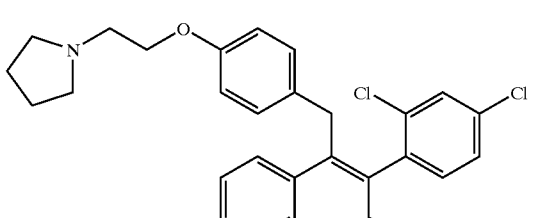 | 0.32 | 5.4 | 0.69 |

Accordingly, the in vitro results of Examples 8–10 as illustrated in Table 2 above, show that the benzopyranone compounds of the present invention are useful for the treatment or prevention of bone-resorbing diseases and various cancers.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference in their entirety.

What is claimed is:

1. A compound having the structure:

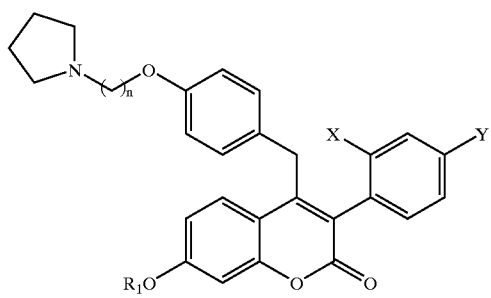

(I)

or a pharmaceutically acceptable salt thereof, wherein:

n is 2, 3 or 4;

$R_1$ is hydrogen, C(=O)$R_2$, C(=O)O$R_2$, C(=O)NH$R_2$, C(=O)N$R_2R_3$, or S(=$O_2$)N$R_2R_3$;

$R_2$ and $R_3$ are independently $C_{1-8}$alkyl, $C_{6-12}$aryl, $C_{7-12}$arylalkyl, or a five- or six-membered heterocycle containing up to two heteroatoms selected from O, N$R_4$ and S(O)$_q$, wherein each of the above groups are optionally substituted with one to three substituents independently selected from $R_5$ and q is 0, 1 or 2;

$R_4$ is hydrogen or $C_{1-4}$alkyl;

$R_5$ is hydrogen, halogen, hydroxy, $C_{1-6}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$aryl, $C_{7-12}$aralkyl, COOH, CN, CONHO$R_6$, $SO_2$NH$R_6$, $NH_2$, $C_{1-4}$alkylamino, $C_{1-4}$dialkylamino, NHSO$_2R_6$, $NO_2$, or a five- or six-membered heterocycle, where each occurrence of $R_6$ is independently $C_{1-6}$alkyl;

X is hydrogen, halogen or trifluoromethyl; and

Y is halogen or trifluoromethyl.

2. The compound of claim 1 wherein Y is trifluoromethyl.
3. The compound of claim 1 wherein Y is chloro.
4. The compound of claim 1 wherein X is trifluoromethyl.
5. The compound of claim 1 wherein X is chloro.
6. The compound of claim 1 wherein X is hydrogen.
7. The compound of claim 1 wherein $R_1$ is hydrogen.
8. The compound of claim 1 wherein $R_1$ is C(=O)$R_2$, C(=O)O$R_2$, C(=O)NH$R_2$, C(=O)N$R_2R_3$, or S(=$O_2$)N$R_2R_3$.
9. The compound of claim 1 wherein n is 2.
10. The compound of claim 1 wherein n is 3 or 4.

11. The compound of claim 1 having the structure:

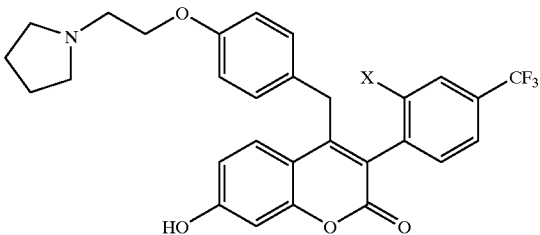

or a pharmaceutically acceptable salt thereof.

12. The compound of claim 1 having the structure:

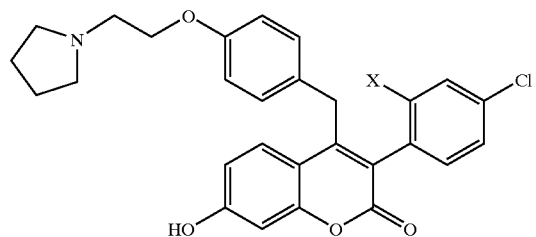

or a pharmaceutically acceptable salt thereof.

13. The compound of claim 11 having the structure:

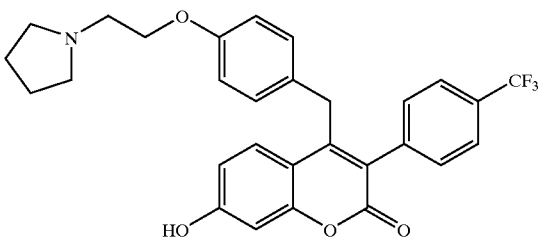

or a pharmaceutically acceptable salt thereof.

14. The compound of claim 11 having the structure:

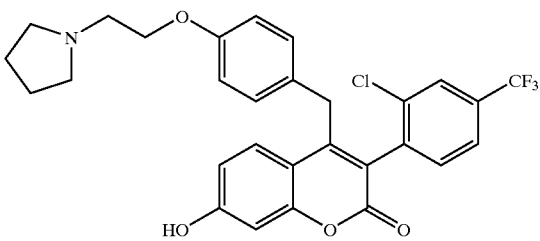

or a pharmaceutically acceptable salt thereof.

15. The compound of claim 11 having the structure:

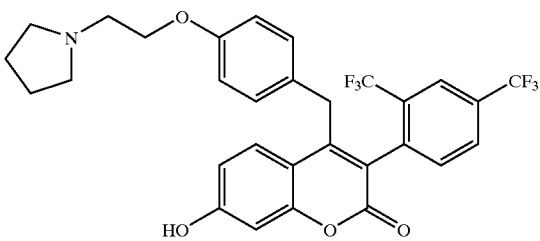

or a pharmaceutically acceptable salt thereof.

16. The compound of claim 12 having the structure:

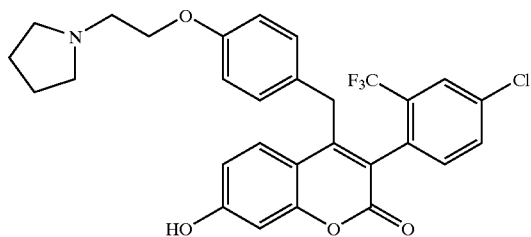

or a pharmaceutically acceptable salt thereof.

17. The compound of claim 12 having the structure:

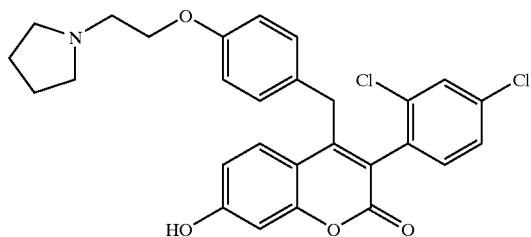

or a pharmaceutically acceptable salt thereof.

18. The compound of claim 12 having the structure:

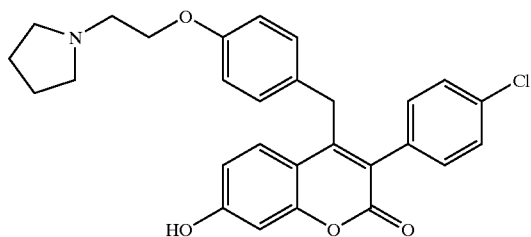

or a pharmaceutically acceptable salt thereof.

19. The compound or a pharmaceutically acceptable salt of the compound of claim 1, wherein n=2 and:

| | | |
|---|---|---|
| $R_1 = H$, | $X = F$, | $Y = CF_3$; |
| $R_1 = H$, | $X = Br$, | $Y = CF_3$; |
| $R_1 = H$, | $X = I$, | $Y = CF_3$; |
| $R_1 = C(=O)CH_3$, | $X = H$, | $Y = CF_3$; |
| $R_1 = C(=O)CH_3$, | $X = Cl$, | $Y = CF_3$; |
| $R_1 = C(=O)CH_3$, | $X = Br$, | $Y = CF_3$; |
| $R_1 = C(=O)CH_3$, | $X = I$, | $Y = CF_3$; |
| $R_1 = C(=O)CH_3$, | $X = CF_3$, | $Y = CF_3$; |
| $R_1 = C(=O)CH_3$, | $X = F$, | $Y = CF_3$; |
| $R_1 = H$, | $X = F$, | $Y = Cl$; |
| $R_1 = H$, | $X = Br$, | $Y = Cl$; |
| $R_1 = H$, | $X = I$, | $Y = Cl$; |
| $R_1 = C(=O)CH_3$, | $X = H$, | $Y = Cl$; |
| $R_1 = C(=O)CH_3$, | $X = Cl$, | $Y = Cl$; |
| $R_1 = C(=O)CH_3$, | $X = F$, | $Y = Cl$; |
| $R_1 = C(=O)CH_3$, | $X = Br$, | $Y = Cl$; |
| $R_1 = C(=O)CH_3$, | $X = I$, | $Y = Cl$; or |
| $R_1 = C(=O)CH_3$, | $X = CF_3$, | $Y = Cl$. |

20. A composition comprising a compound of claim 1, or a pharmaceutically acceptable salt of the compound; and a pharmaceutically acceptable carrier or vehicle.

21. A method for inhibiting a cytokine in a patient, comprising administering to a patient in need thereof an effective amount of a compound of claim 1, or a pharmaceutically acceptable salt of the compound.

22. The method of claim 21 wherein the cytokine is IL-6.

23. The method of claim 21 wherein the cytokine is GM-CSF.

24. A method for treating a bone-resorbing disease in a patient, comprising administering to a patient in need thereof an effective amount of a compound of claim 1, or a pharmaceutically acceptable salt of the compound.

25. The method of claim 24 wherein the bone-resorbing disease is osteoporosis.

26. The method of claim 24 wherein the bone-resorbing disease is metastatic bone cancer, osteolytic lesions with an orthopedic implant, Paget's disease, hypercalcemia or bone loss associated with hyperparathyroidism.

27. A method for treating cancer in a patient, comprising administering to a patient in need thereof an effective amount of a compound of claim 1, or a pharmaceutically acceptable salt of the compound.

28. The method of claim 27 wherein the cancer is breast cancer, prostrate cancer, colon cancer, endometrial cancer, multiple myeloma, renal cell carcinoma, or cervical carcinoma.

29. A method for treating arthritis in a patient, comprising administering to a patient in need thereof an effective amount of a compound of claim 1, or a pharmaceutically acceptable salt of the compound.

30. The method of claim 29 wherein the arthritis is rheumatoid arthritis.

31. The method of claim 29 wherein the arthritis is adjuvant-, collagen-, bacterial- or antigen-induced.

32. A method for treating an estrogen-related condition in a patient, comprising administering to a patient in need thereof an effective amount of a compound of claim 1, or a pharmaceutically acceptable salt of the compound.

33. The method of claim 32 wherein the estrogen-related condition is breast cancer, osteoporosis, endometriosis, cardiovascular disease, hypercholesterolemia, prostatic hypertrophy, prostatic carcinomas, obesity, cataracts, hot flashes, skin effects, mood swings, memory loss, prostate cancer, menopausal syndromes, type-II diabetes, Alzheimer's disease, urinary incontinence, GI tract conditions, spermatogenesis, vascular protection after injury, endometriosis, learning and memory, CNS effects, plasma lipid levels, acne, hirsutism, solid cancers, multiple myeloma, lymphoma, or adverse reproductive effects associated with exposure to environmental chemicals or natural hormonal imbalances.

* * * * *